US012667252B2

(12) United States Patent
Solenski et al.

(10) Patent No.: US 12,667,252 B2
(45) Date of Patent: Jun. 30, 2026

(54) SYSTEM AND METHOD FOR VISUAL FIELD RAPID ASSESSMENT

(71) Applicant: University of Virginia Patent Foundation, Charlottesville, VA (US)

(72) Inventors: Nina J. Solenski, Charlottesville, VA (US); Jeffrey Ashe Allende, Henrico, VA (US); Arjun Dirghangi, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 975 days.

(21) Appl. No.: 17/794,422

(22) PCT Filed: Nov. 24, 2020

(86) PCT No.: PCT/US2020/062023
§ 371 (c)(1),
(2) Date: Jul. 21, 2022

(87) PCT Pub. No.: WO2021/154375
PCT Pub. Date: Aug. 5, 2021

(65) Prior Publication Data
US 2023/0072559 A1      Mar. 9, 2023

Related U.S. Application Data

(60) Provisional application No. 62/968,254, filed on Jan. 31, 2020.

(51) Int. Cl.
*A61B 3/024*         (2006.01)
*A61B 3/00*          (2006.01)

(52) U.S. Cl.
CPC ............ *A61B 3/024* (2013.01); *A61B 3/0008* (2013.01)

(58) Field of Classification Search
CPC ................................ A61B 3/024; A61B 3/008
(Continued)

(56) References Cited

U.S. PATENT DOCUMENTS 5,583,795 A  *  12/1996  Smyth .................. A61B 3/0025
                                                  702/92
5,946,075 A      8/1999  Horn
(Continued)

FOREIGN PATENT DOCUMENTS

WO            9529627 A1    11/1995
WO    WO-2017134275 A1  *  8/2017   ........ G01M 11/0221

OTHER PUBLICATIONS

Dodgson, Neil A., "Variation and Extrema of Human Interpupilla.ry Distance", Proceedings of SPIE—The International Society for Optical Engineering, vol. 5291, Jan. 2004, pp. 36-46.
(Continued)

*Primary Examiner* — Sharrief I Broome
(74) *Attorney, Agent, or Firm* — Robert J. Decker

(57) ABSTRACT

System and associated methods of use for rapid assessment of visual field integrity. In one embodiment, the device comprises a frame that rests near a patient's eyes with pinpoint lights or mechanical stimuli that act as visual stimuli mounted at locations within the frame and in the patient's peripheral visual field. A vantage point in front of the frame allows an operator to view the patient's eyes during assessment, enabling the operator to maximize the accuracy during both in person and telemedicine assessments. The lights or mechanical stimuli are positioned such that they are visible to patients with a wide range of interpupillary distances, enabling the use of a single-size device for all patients.

61 Claims, 22 Drawing Sheets

(58) Field of Classification Search
USPC ........................................................ 351/224
See application file for complete search history.

(56)                    References Cited

U.S. PATENT DOCUMENTS

| | | | |
|---|---|---|---|
| 6,033,076 A | 3/2000 | Braeuning et al. |
| 6,299,632 B1 | 10/2001 | Jaillet |
| 6,475,162 B1 | 11/2002 | Hu |
| 7,220,000 B2 | 5/2007 | Alster et al. |
| 7,278,742 B2 | 10/2007 | Manahilov |
| 7,309,315 B2 | 12/2007 | Kullok et al. |
| 7,594,728 B2 | 9/2009 | Seal et al. |
| 8,583,223 B2 | 11/2013 | Maddess et al. |
| 8,807,753 B2 | 8/2014 | Maddess et al. |
| 8,851,678 B2 | 10/2014 | Pelah et al. |
| 8,931,905 B2 | 1/2015 | Lewis |
| 9,619,613 B2 | 4/2017 | Meyer et al. |
| 9,625,989 B2 | 4/2017 | Wilson et al. |
| 9,629,538 B2 | 4/2017 | Wang |
| 9,823,808 B2 | 11/2017 | Crain et al. |
| 9,848,771 B2 | 12/2017 | Maddess et al. |
| 9,895,057 B2 | 2/2018 | Tumlinson |
| 10,064,548 B2 | 9/2018 | Maddess et al. |
| 10,143,367 B2 | 12/2018 | Gonzalez de la Rosa |
| 10,178,948 B2 | 1/2019 | Liu et al. |
| 2007/0038142 A1 | 2/2007 | Todd et al. |
| 2011/0066586 A1 | 3/2011 | Sabel et al. |
| 2012/0212414 A1* | 8/2012 | Osterhout ............... G06F 1/163 |
| | | 345/158 |
| 2015/0235457 A1* | 8/2015 | Schowengerdt ...... G02F 1/1334 |
| | | 345/633 |
| 2017/0007450 A1* | 1/2017 | Samec .................. G06T 19/006 |
| 2017/0038608 A1* | 2/2017 | Cabeza-Guillen ... G02C 13/005 |
| 2020/0041797 A1 | 2/2020 | Samec et al. |

OTHER PUBLICATIONS

WIPO, "International Search Report and Written Opinion of the International Searching Authority", International Patent Application No. PCT/US2020/062023, mailed Feb. 9, 2021, 19 pages.

* cited by examiner

SYSTEM AND METHOD FOR VISUAL FIELD RAPID ASSESSMENT

The present application is a national stage filing of International Application No. PCT/US2020/062023, filed Nov. 24, 2020, which claims benefit of priority under 35 U.S.C § 119 (e) from U.S. Provisional Application Ser. No. 62/968,254, filed Jan. 31, 2020, entitled "System, Method and Computer Readable Medium for Visual Field Rapid Assessment"; the disclosures of which are hereby incorporated by reference herein in their entirety.

CROSS REFERENCE TO RELATED APPLICATIONS

The present application claims benefit of priority under 35 U.S.C § 119 (e) from U.S. Provisional Application Ser. No. 62/968,254, filed Jan. 31, 2020, entitled "System, Method and Computer Readable Medium for Visual Field Rapid Assessment"; the disclosure of which is hereby incorporated by reference herein in its entirety.

FIELD OF INVENTION

The present disclosure relates generally to monitoring and delivering in-situ real-time personalized intervention(s) for a patient and/or caregiver. More particularly, the present disclosure relates to a system and associated methods of use for rapid assessment of a patient's visual field integrity based on detection of visual stimuli.

BACKGROUND

During emergency medical consults, a rapid, accurate assessment of visual field integrity is often required for the diagnosis and assessment of ocular trauma and head trauma, including the detection of brain injury consistent with a stroke or other event. The rapid identification of visual field deficits is critical for rapid diagnosis and the administration of time-sensitive therapies. The initial stroke evaluation, also known as the NIH Stroke Scale (NIHSS), quantifies the severity of the stroke on a scale from 0 to 42, of which visual field integrity accounts for three "points." A patient must score at least a 6 to be eligible for transfer to a tertiary care stroke center for thrombectomy (invasive intracranial clot retrieval). Such stroke treatment is highly time-sensitive, as every minute of delay leads to greater damage to the affected area of the brain, which is often irreversible.

A traditional approach to visual field integrity assessment is a confrontational visual fields test, typically performed by ophthalmologists or other trained medical providers. The test is performed by covering one eye of the patient and raising a certain number of fingers in the peripheral visual field while the patient maintains a steady, forward gaze. Accurate assessment of visual field integrity using the confrontational visual fields test requires physical proximity to the patient. This proximity is limited or impossible in remote telemedicine consultations, including live telestroke consultations where proper diagnosis is time-sensitive. This leads to misidentification of visual field deficits, which can alter the diagnosis and treatment a patient receives. Additionally, accurate administration of the test is difficult for physicians, nurses, paramedics, and other providers who are untrained or inexperienced in screening patients for visual field deficits through a confrontational visual fields test. Training for nurses is often not practical due to the high number and high turnover rate of nurses in emergency departments. Therefore, there exists a need for a device that facilitates rapid, accurate, and repeatable screening for gross visual field deficits during in-person and telemedicine consultations.

An alternative approach to visual field assessment involves the use of perimetry machines, such as the Humphrey Field Analyzer or the Goldmann Perimeter. However, even these devices are unsatisfactory for acute stroke consults or other specialty consults, whether in-person or remote, because they require significant time to diagnose visual field deficits, and even short delays in the treatment of stroke can result in permanent brain damage. Perimetry machines are also relatively expensive and so bulky that they require the patient to sit upright and place their head into an enclosed compartment, which may not be feasible for patients with limited mobility, such as patients with ocular trauma or head trauma. These devices are particularly unsatisfactory for remote consults, as patients may be located in rural areas where their attending medical provider may not have access to these specialized devices. As a consequence of their size, perimetry devices are also inconvenient to thoroughly disinfect for use between patients. Such devices also prevent the operator from directly observing the stimuli presented to the patient, a necessary form of verification when the activation order of the stimuli is random or otherwise unknown to the operator. Similarly, perimetry devices do not allow the operator to monitor the patient to ensure that the patient maintains a straightforward gaze and does not engage a reflexive eye movement toward the target appearing in the visual periphery. This is important because acute stroke consults specifically call for assessment of peripheral visual fields, as central vision is likely to remain intact during and subsequent to a stroke. Finally, perimetry devices do not account for the fact that the exact location of a patient's peripheral visual field may differ from person to person, based on varying interpupillary distances (IPDs).

Therefore, there is a need in the art for a rapid, accurate, standardized and repeatable visual field integrity assessment device and associated method of use that is faster, cheaper, less-bulky, and easy to disinfect. Additionally, there is a need in the art for a device and associated method that allows for directly observing the stimuli presented to the patient and monitoring the patient's straightforward gaze. To resolve the above issues, the inventors developed a Visual Fields Rapid Assessment Device (VRAD) and associated method of use.

SUMMARY OF ASPECTS OF EMBODIMENTS OF THE PRESENT INVENTION

The Visual Fields Rapid Assessment Device (VRAD) is a robust, low-cost tool that allows providers to rapidly assess visual field integrity in patients during in-person and remote consultations. In one embodiment, the VRAD is comprised of a frame or lens that rests near the eyes, with pinpoint lights or mechanical stimuli that act as visual stimuli mounted at locations within the frame or lens, wherein the lights or mechanical stimuli are configured to be in communication with a processor or controller, such as a microcontroller, servomotor, a computer, or a circuit board. In some embodiments, the processor or controller may be included in a kit configured to be used with the device. In addition, the processor or controller may be powered by a power source and/or linked to a computer interface. The system, processor or controller, and computer interface may interface through various means, such as hard-wired or wireless communication. The pinpoint lights or mechanical stimuli may be placed anywhere on the frame and/or lens or surface as desired or required. One embodiment of the device will have pinpoint lights or mechanical stimuli positioned such that the stimuli will be in the peripheral visual field of patients with a wide range of interpupillary distances (IPDs) (e.g., between 50 and 75 mm), enabling the use of a single-size device for all patients. In this embodiment, the exact placement of the lights or mechanical stimuli will be at least 24 degrees from the center of the pupil to ensure that the stimulus will not be seen in the central vision. In other embodiments, the lights or mechanical stimuli could be approximately 23 to 25 degrees, 22 to 26 degrees, 18 to 30 degrees, or 24 to 34 degrees from the center of the pupil.

During a remote stroke ("telestroke") consultation during which visual field screening is needed, an operator will take the device and place it onto the patient's face. The nurse or telehealth provider will instruct the patient to look straight at the camera and indicate when they see a light blink (or activity by a mechanical stimuli), either by pointing to the region lit (or activated), or saying "right upper", "left lower", etc. During a trial, the operator or provider must monitor the patient's eyes for a straightforward gaze and attend to the patient for indication that the patient saw a stimulus. Either one or two stimuli will flash simultaneously during an assessment, and the patient reports the number of stimuli seen to test for extinction. The lights or mechanical stimuli are programmed such that each quadrant of peripheral vision is tested at least once, in random order and at random intervals. If the patient accurately identifies the blink while looking ahead, the trial is successful and the associated quadrant of the visual field is deemed functional. In the second phase of the assessment, each eye is individually tested. If the patient fails to see a certain light blink (or see activity by a mechanical stimuli) across multiple trials, the patient will have failed the screening test and is scored either a 1, 2, or 3 on the NIHSS depending on the extent of the visual deficit, or is referred to for a more comprehensive visual field deficit testing.

Ultimately, the clinical significance of the VRAD is the standardization of the confrontational visual fields test, a subjective procedure, which eliminates the need for specialized training for nurses and other providers during in-person and telemedicine consults. The VRAD is advantageous in that the device is inexpensive, robust, easy to disinfect for use between patients, and usable by patients with limited mobility.

An aspect of an embodiment of the present invention provides, but not limited thereto, a system for performing rapid, interactive screening of visual fields of a patient. The system may comprise: a frame having a front and a back, wherein the back of the frame directionally faces a patient and the front of the frame is opposite the back of the frame and directionally faces one or more operators; and wherein the frame is configured to allow a vantage point adjacent to and in front of the front of the frame to allow direct observation of one or both eyes of the patient. The system may further comprise a plurality of lights or mechanical stimuli in mechanical communication with the frame, wherein upon activation of the plurality of lights or the mechanical stimuli, the plurality of lights or the mechanical stimuli are directly visible by the patient and the one or more operators, and wherein the plurality of lights or the mechanical stimuli are disposed in a position, wherein the position allows for the testing of a patient's visual fields. Furthermore, the plurality of lights or the mechanical stimuli are configured to be in hard-wired or wireless communication with a processor or controller and the plurality of lights or the mechanical stimuli are configured to activate in a specified order, wherein the specified order is in accordance with a testing protocol.

An aspect of an embodiment of the present invention provides, but not limited thereto, a method for performing rapid, interactive screening of visual fields. The method may comprise: providing a system for performing the rapid, interactive screening of visual fields on a patient, wherein the system is configured to be placed on the patient such that one or more of the patient's eyes are directly observable by one or more operators relative to a vantage point located in front of the patient; providing instructions to the patient for the patient to provide feedback when one or more lights or mechanical stimuli on the system are activated, wherein the one or more lights or the mechanical stimuli are disposed in a position, wherein the position allows for the testing of a patient's visual fields; and activating the lights or the mechanical stimuli, using a processor or controller, in one or more specified orders, wherein the one or more specified orders is in accordance with a testing protocol. Furthermore, the system is configured to allow the operator to be positioned at the vantage point to allow the operator to substantially simultaneously observe: one or both of the patient's eyes; one or more of the lights or the mechanical stimuli activated; and the feedback provided by the patient.

An aspect of an embodiment of the present invention provides, but not limited thereto, a method for performing rapid screening of visual field deficits of a patient. The method comprises: instructing the patient to provide feedback when one or more visual stimuli are visible to the patient; using an apparatus to display one or more visual stimuli in a peripheral visual field quadrant to the patient, while one or both of the patient's eyes are directly observable by an operator; and displaying the one or more visual stimuli in at least one of the remaining quadrants in a specified order, wherein the specified order in accordance with a testing protocol. Furthermore, the operator substantially simultaneously observes: one or both of the patient's eyes; one or more of the stimuli; and the feedback provided by the patient; and further wherein the operator evaluates a result of the observations for one or more potential visual field deficits.

An aspect of an embodiment of the present invention provides, but not limited thereto, a system and associated methods of use for rapid assessment of visual field integrity. In one embodiment, the device comprises a frame that rests near a patient's eyes with pinpoint lights or mechanical stimuli that act as visual stimuli mounted at locations within the frame and in the patient's peripheral visual field. A vantage point in front of the frame allows an operator to view the patient's eyes during assessment, enabling the operator to maximize the accuracy during both in person and telemedicine assessments. The lights or mechanical stimuli are positioned such that they are visible to patients with a wide range of interpupillary distances, enabling the use of a single-size device for all patients.

The invention itself, together with further objects and attendant advantages, will best be understood by reference to the following detailed description, taken in conjunction with the accompanying drawings.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

Figure 15:
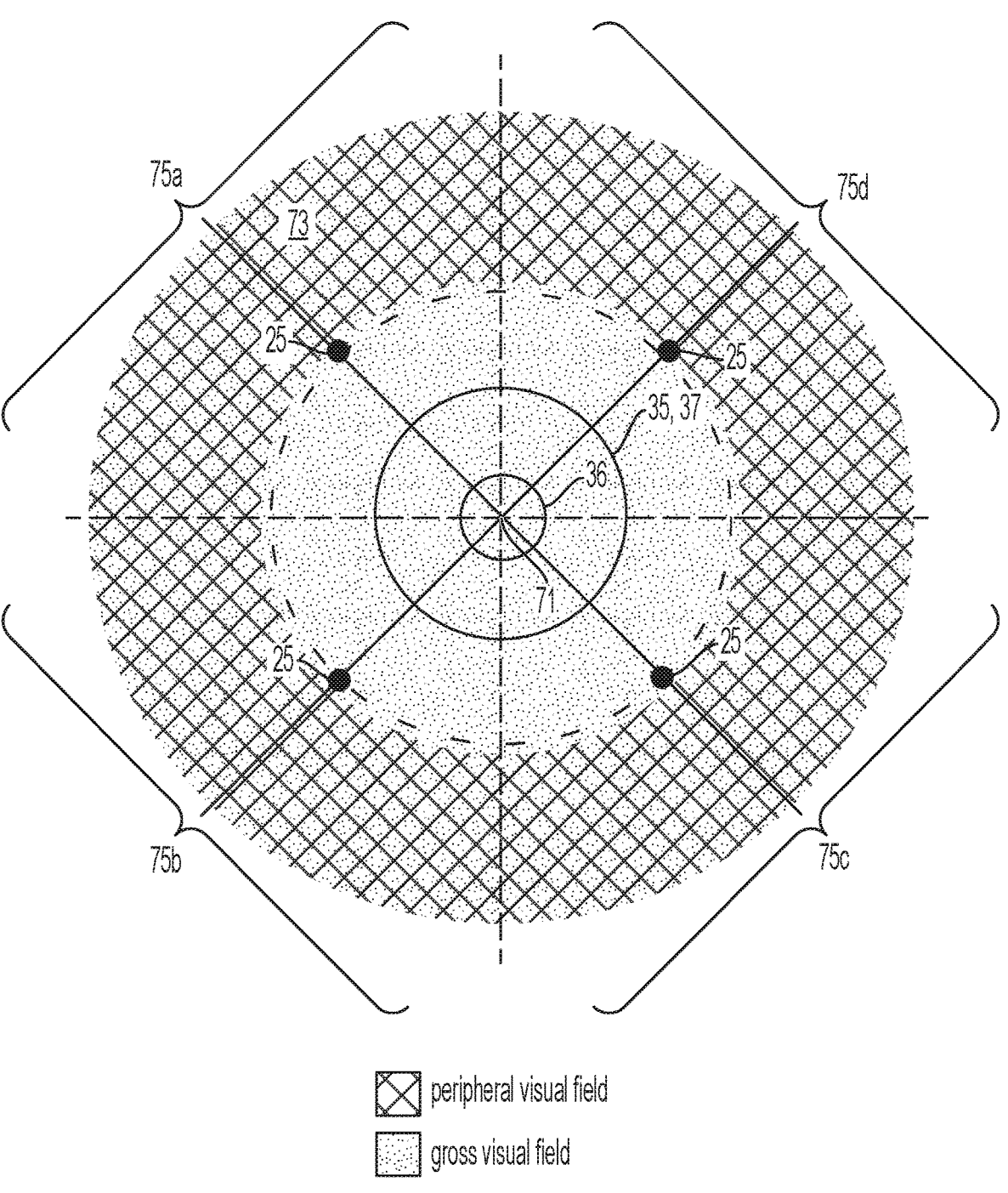
FIG. 15 is a diagram illustrating an example of peripheral and gross visual fields that can be tested by embodiments of the present invention.

The Visual Field Rapid Assessment Device (VRAD) may be used to, among other things, facilitate the rapid, accurate assessment of gross visual field deficits by standardizing the relative position of the visual stimuli 25 associated with confrontational visual field testing, although it should be appreciated that additional visual field testing can be performed using the VRAD system. The stimuli 25 are presented in the peripheral region of the visual field 73 of a patient 19 as shown in FIG. 15.

Figures 2A, 2B:
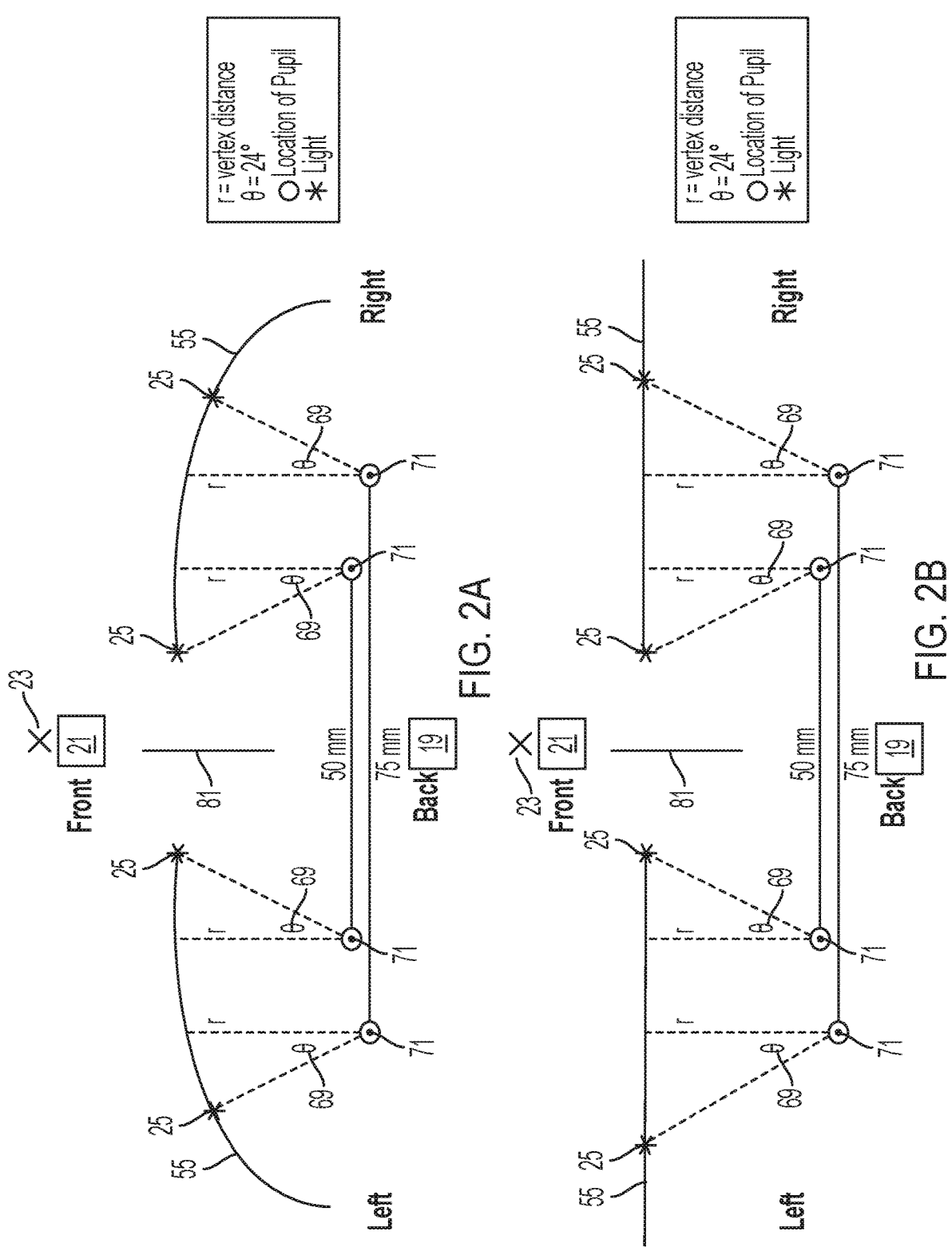
FIG. 2A is a schematic diagram illustrating the relative position of a patient and an operator; relative locations of stimuli, based on a range of interpupillary distances (IPDs), positioned on a curved frame, lens, or surface; and assumed vertex distance where two sets of pupil locations (wide and narrow) represent an exemplary, non-limiting, range of interpupillary distances (IPDs) for a particular embodiment.
FIG. 2B is a schematic diagram illustrating the relative position of a patient and an operator; relative locations of lights or mechanical stimuli, based on a range of interpupillary distances (IPDs), positioned on a straight frame, lens, or surface; and assumed vertex distance where two sets of pupil locations (wide and narrow) represent an exemplary, non-limiting, range of interpupillary distances (IPDs).

Referring to FIGS. 2A-2B, for example, when using the device, the operator 21 would only need to ask the patient 19 to indicate whether they see a stimulus 25 or to indicate how many stimuli 25 that they are able to see, monitor the patient's eyes 35, 37 (not shown) from a vantage point 23 adjacent to and in front of the device for a straightforward gaze, and attend to the patient 19 for indication that the patient 19 saw a stimulus 25. In one embodiment, the operator 21 determines whether the feedback provided by the patient 19 indicates the patient 19 observed one or more lights or mechanical stimuli 25 activated.

Patients 19 may include but are not limited to individuals with symptoms and/or pre-diagnosis of stroke, ocular trauma, head trauma, brain injury, glaucoma, brain tumor, pituitary disease, or neurological deficit. It should be appreciated that patients 19 may also include individuals who are not seeking treatment or diagnosis of a visual or neurological deficit but are instead seeking a visual deficit evaluation such as an evaluation for a driver's exam.

Figure 1:
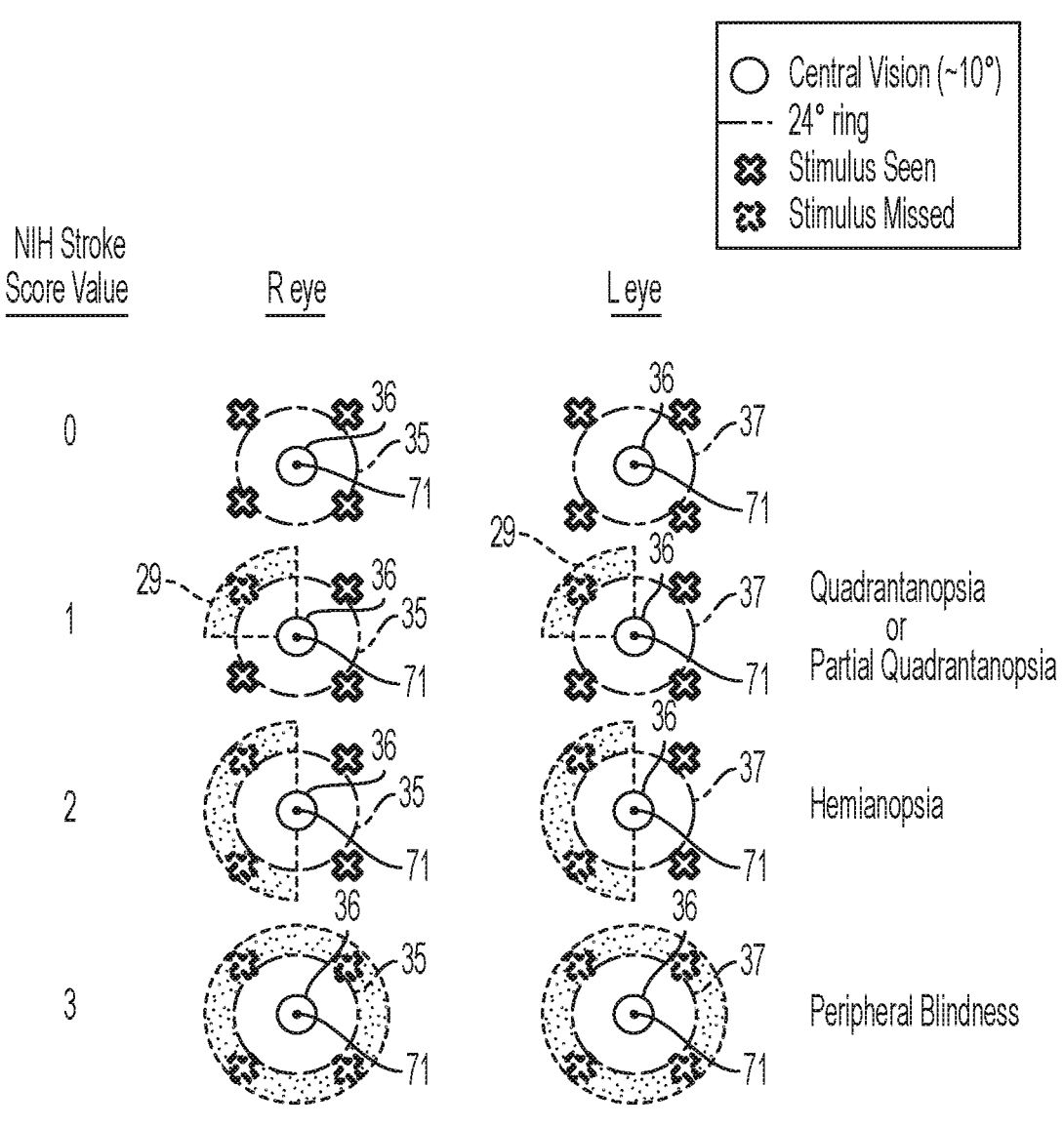
FIG. 1 is a schematic diagram illustrating common visual field deficits incurred in neurologic injury intended to be identified using one embodiment of the present invention.
Figure 16:
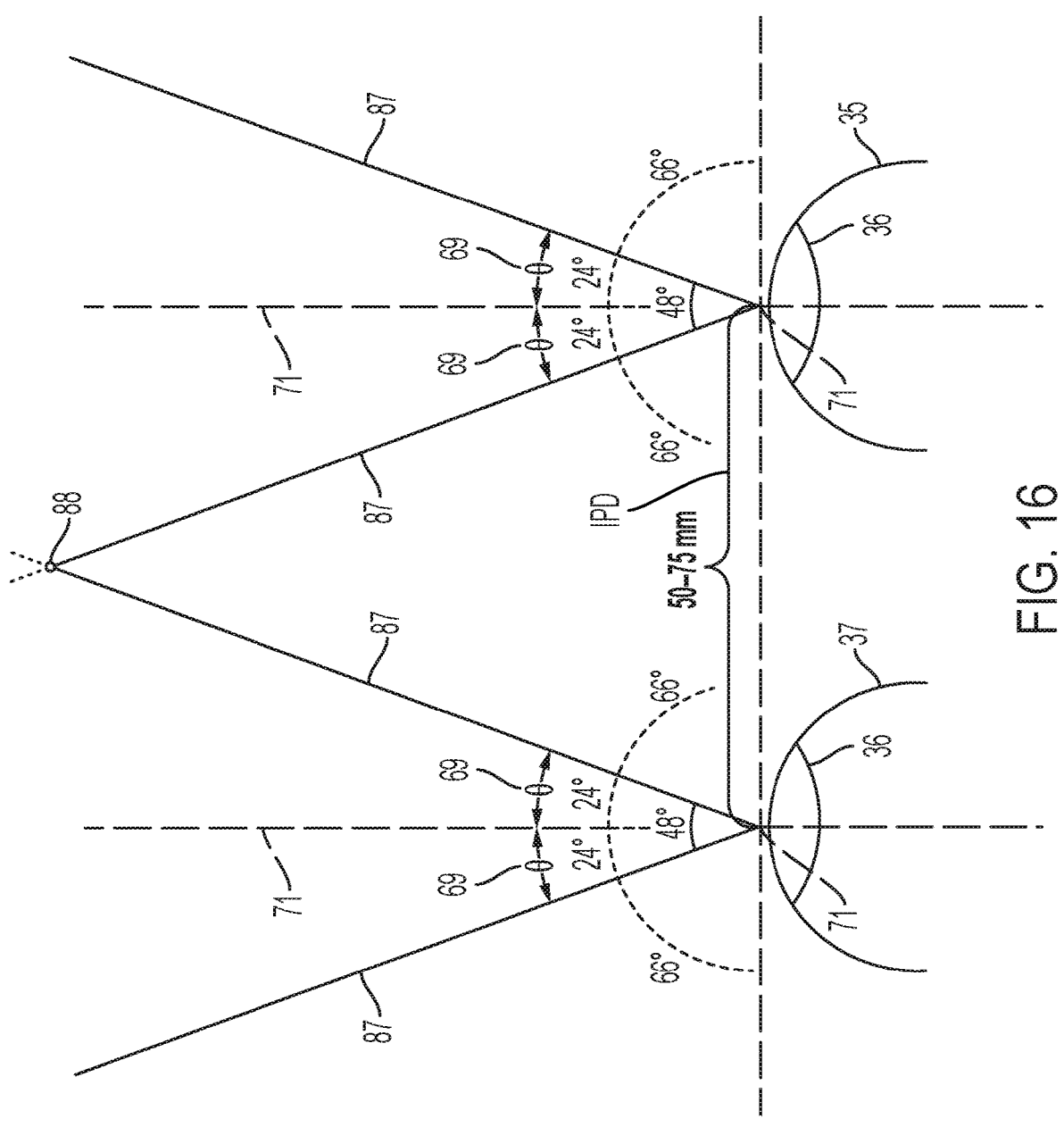
FIG. 16 is a diagram illustrating a top view of a patient's eyes with an example degree range and varying vertex distance where positions of stimuli are established based on a range of interpupillary distances (IPDs) (e.g., between 50 and 75 mm).
Figure 17:
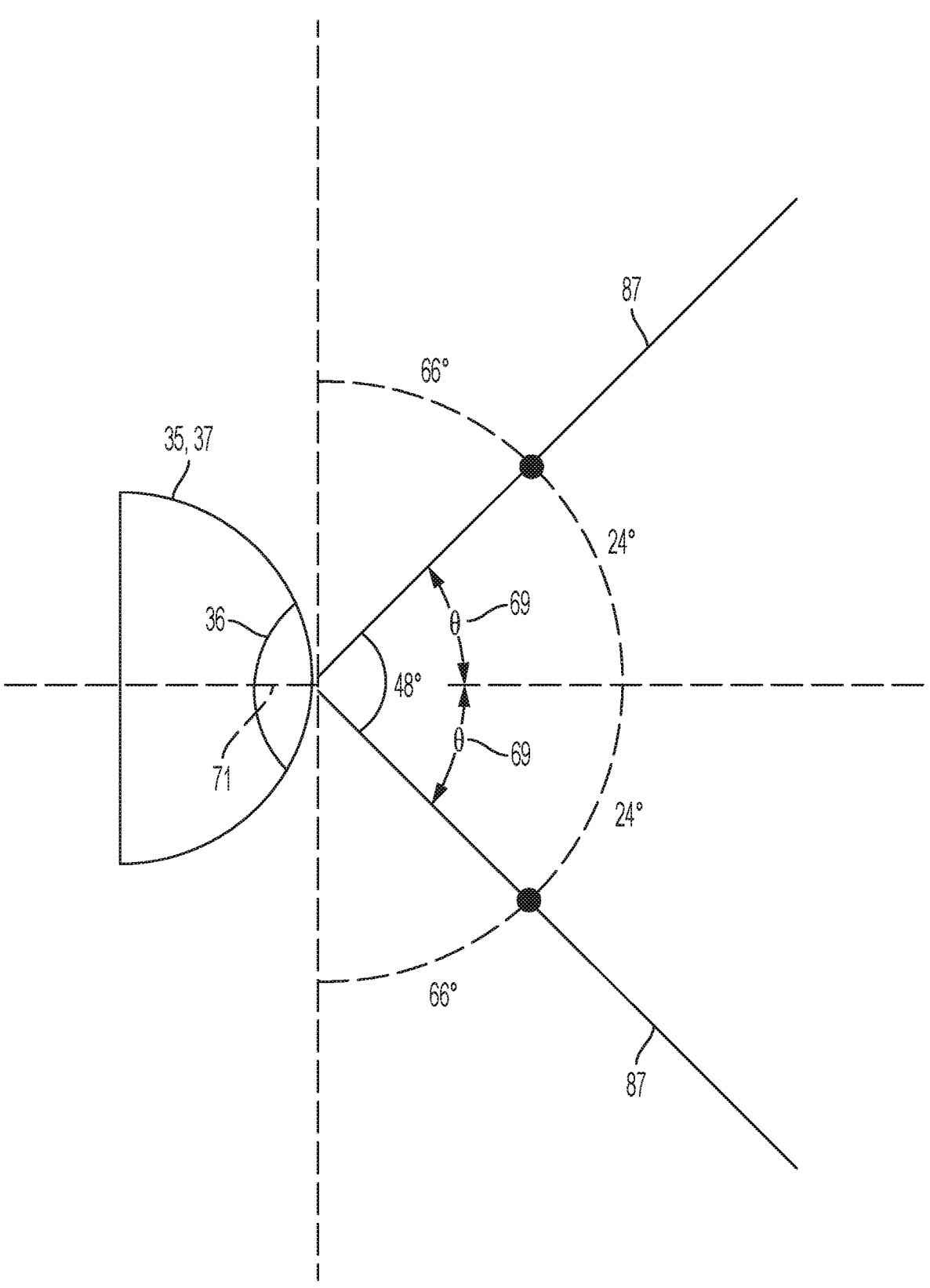
FIG. 17 is a diagram illustrating a side view of a patient's eye with an example degree range and varying vertex distance where positions of stimuli are established based on a range of interpupillary distances (IPDs) (e.g., between 50 and 75 mm).
Figure 21:
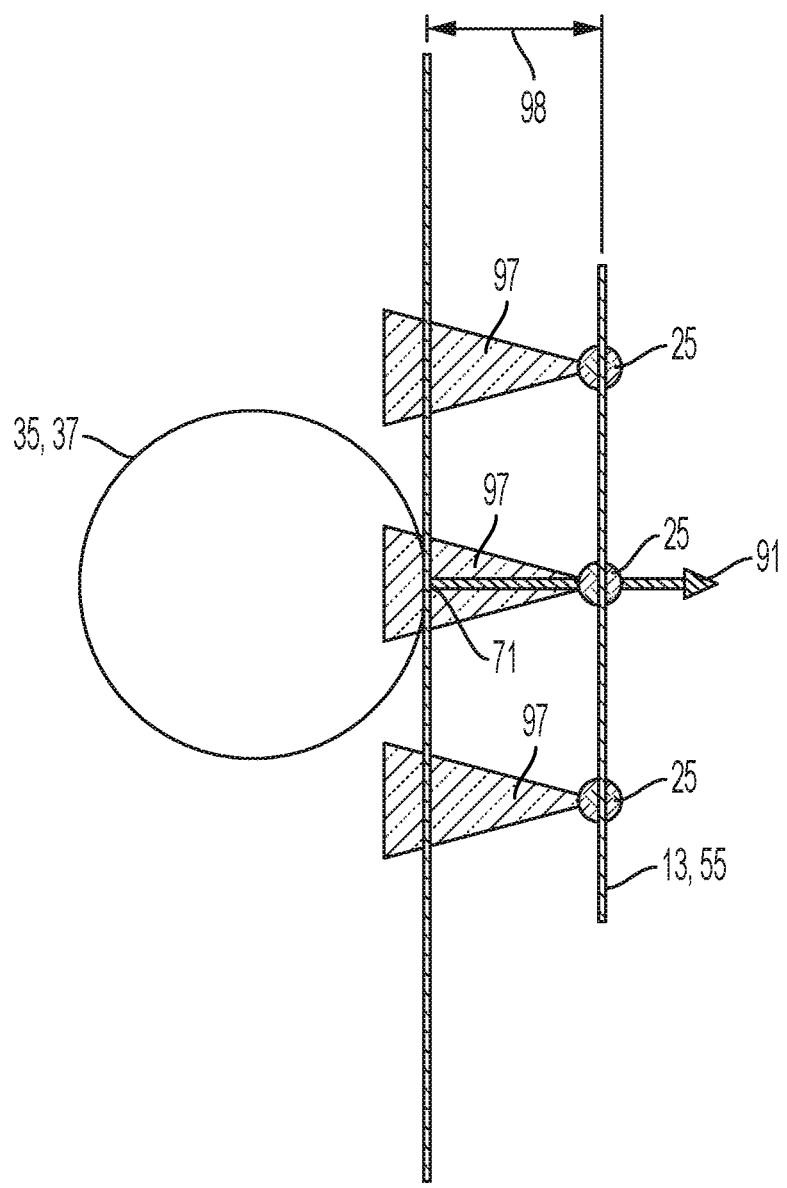
FIG. 21 is a schematic diagram illustrating the distance between the pupil center and the placement of the stimuli on a lens, surface, or frame of the present invention.

Referring to FIGS. 1, 16, and 17, for example, the stimuli 25 are positioned along a line 87 corresponding to a degree range 69 to identify gross visual field deficits, particularly those associated with neurological or visual deficits such as quadrantanopsia, partial quadrantanopsia, hemianopsia, and peripheral blindness. Referring to FIG. 21, for example, the stimuli 25 are positioned on a straight or curved frame 13 or associated lens or surface 55 at a sufficient distance, 98, to allow for the testing of a patient's visual fields. A vector 91 pointing outwards from the patient's pupil center 71 represents a patient's straightforward gaze. In an embodiment, the frame 13 or lens 55 is positioned from the patient's pupil center 71 (traveling along the pupil center axis, i.e., orthogonal direction from the pupil center 71) at a distance (98) of at least about 12 mm. In other embodiments, the distance 98 may include, but is not limited to, any of the following: at least about 15 mm; between and inclusive of about 12 and about 15 mm; between and inclusive of about 10 and about 20 mm; between and inclusive of about 10 and about 12 mm; between and inclusive of about 1 and about 6 mm; between and inclusive of about 6 and about 10 mm; between and inclusive of about 20 and about 40 mm; between and inclusive of about 1 and about 40 mm; between and inclusive of about 40 and about 56 mm; between and inclusive of about 56 and about 84 mm; or between and inclusive of about 84 and about 138 mm. In an embodiment, the degree ranges may be less than or greater than the ranges provided. The frame 13 or lens/surface 55 can be moved closer or farther from the patient 19 by either adjusting the length of the temple 43 (not shown) or changing the location of the plurality of lights or the mechanical stimuli 25 relative to the patient 19 or the frame 13 or lens/surface 55. For example, the temple 43 (not shown) may include a telescopic device to extend or retract so as to change the length of the temple 43 to affect the distance 98. Similarly, the nasion brace 41 (not shown), or a nose bridge (not shown) or other components of the system may have a telescopic device or the like to adjust size. Also, the frame 13, temple 79, lens or surface 55, or other components may be provided in different sizes. Other devices or mechanisms on the temple (or other components) may be implemented to alter the length of the temple 43 (or the other components) thus changing the length of the distance 98. Alternatively, the profile of the nasion brace 41 may be changed to alter the distance 98 of the frame 13 or lens or surface 55 to the patient 19 to effect the distance 98. Still yet, extensions or arms may be implemented with the plurality of lights or mechanical stimuli 25 (or other components) so as to change the distance 98 from the patient 19 to frame 13 or lens or surface 55. Also, the distance 98 may need to be altered so as to accommodate the tolerance of the patient 19. In an embodiment, the distance (98) may be less than or greater than the ranges provided.

Referring to FIG. 16, the lines 87 moving towards each other nasally would overlap at an intersection point 88 before the line 87 heading nasally from the right eye 35 would cross into the left eye's visual fields and the line 87 heading nasally from the left eye 37 would cross into the right eye's visual fields. The intersection point 88 is located at a distance from the patient 19 (not shown) to the intersection point 88. A separate distance 98 (not shown) is the distance between the patient's pupil center 71 and the frame 13 or lens/surface 55 towards the one or more operators 21 in an orthogonal direction. FIG. 21 provides an illustration of the distance 98 from the frame 13 or lens/surface 55 to the patient's pupil center 71. Still referring to FIG. 16, if the lines 87 continue past the intersection point 88 as indicated in short-dash lines then the device or system 11 would no longer be useful for testing peripheral visual fields because the stimuli would present to the wrong eyes in the patient's central vision. Therefore, beyond the intersection point 88 (or at the intersection point 88) the device or system would no longer be useful for embodiments used to test a patient's peripheral fields. However, it should be appreciated that in some embodiments the stimuli 25 may be positioned on the lines 87 at or beyond the intersection point 88.

Still referring to FIG. 16, in an embodiment the plurality of lights or mechanical stimuli 25 may be configured such that the plurality of lights or mechanical stimuli 25, closest to the nose of the patient 19, are configured to be a specified number of degrees 69, 0, from a pupil center 71 of the eye of the patient 19 for each of second (L) eye 37 and first (R) eye 35 of the patient. The frame 13 may be positioned at a specified orthogonal distance 98 away from the patient's eyes 35, 37 and towards one or more operators 21 in an orthogonal direction from the patient's eyes 35, 37. An overlap or intersection 88 is defined as the point at which the specified number of degrees 69, 0, from a pupil center 71 of the eye of the patient for each the second (L) eye 37 and first eye 35 of the patient 19, and towards the nose of the patient 19 overlaps or intersects. For purposes of peripheral vision, for example, the frame 13 or other components may be configured so that the specified orthogonal distance 98 is less than the distance from the patient 19 to the overlap or intersection 88 and towards the one or more operators 21 in an orthogonal direction.

In another embodiment, for purposes of central vision, for example, the frame 13 or other components may be configured so that the specified orthogonal distance 98 is greater than the distance from the patient 19 to the overlap or intersection 88 and towards the one or more operators 21 in an orthogonal direction. In an embodiment, the system 11 can be configured to test central vision by using a 24-degree angle 69, 0, but using the angle to position the stimuli for the opposite eye in its central vision (somewhere along the short-dash continuation of lines 87). In an embodiment, the same central vision testing could be accomplished by using a smaller angle 69, 0, in the first place and keeping the frame 13 closer to the patient 19. But there may be an advantage to testing central vision farther from the patient 19, particularly if the frame 13 would have to get very close (within about ~1 mm) to the patient's eyes 35, 37.

Still referring to FIG. 16, and given a static degree angle, $\theta$ (69), the smaller the patient's interpupillary distance (IPD) then the smaller the distance 98 (not shown) from the pupil center 71 to the frame 13 or lens/surface 55 (not shown). Conversely, given the same static degree angle, $\theta$ (69), the larger the patient's interpupillary distance (IPD) then the larger the distance 98 (not shown) from the pupil center 71 to the frame 13 or lens/surface 55 (not shown).

The intersection point 88 of the lines 87 is determined by the degree angle, θ (69), and the interpupillary distance (IPD) of the system 11. For example, at a 24-degree angle, θ (69), with interpupillary distance (IPD) of 50 mm, the lines would cross (88) at a distance (98) of about 56.15 mm. By comparison a 24-degree angle, θ (69), with interpupillary distance (IPD) of 75 mm means the lines 87 would cross (88) at a distance (98) of about 84.23 mm. For an 18-degree angle, θ (69), with interpupillary distance (IPD) of 90 mm, the lines would cross (88) at a distance (98) of about 138.50 mm. For instance, the Tangent of θ (69) equals ½ IPD divided by distance (98). Accordingly, distance (98) can be therefore derived. In some embodiments, the interpupillary distance (IPD) of the specific patient-to-be-tested 19 is used rather than the interpupillary distance (IPD) or range of interpupillary distances (IPDs) allowed by the system 11.

Figure 19:
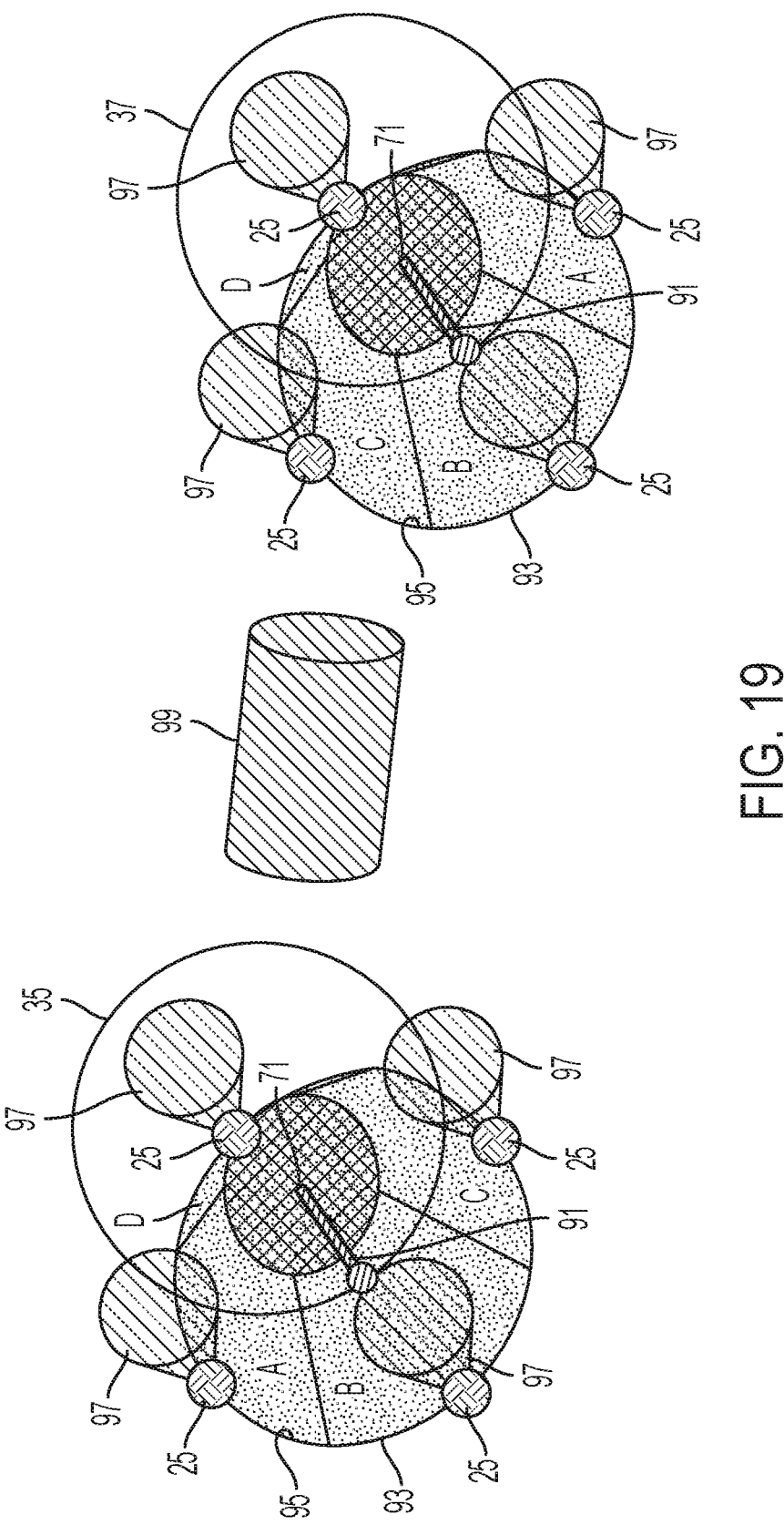
FIG. 19 is a schematic diagram illustrating a coordinate system of one embodiment of the present invention designed using Computer Aided Design to represent the straightforward gaze of the patient, a cone of the degree angle from the expected variance in the location of the patient's pupils projected on an imaginary surface away from the pupils, stimuli on the same imaginary surface projecting individual cones of light towards the patient's eyes, and a cylinder contact point between the device and the patient's nasion.

FIG. 19 illustrates one embodiment of the present invention where the stimuli 25 are positioned at a degree range 69 (not specifically called out) from a patient's pupil center 71 with interpupillary distances (IPDs) between 50 and 75 mm. A vector 91 pointing outwards from the patient's pupil center 71 represents a patient's straightforward gaze, a speckled cone 93 represents the patient's visual fields (designated as 93 having four quadrants, A, B, C and D) where the base 95 of the cone 93 lies on a straight frame 13 (not shown) or associated lens or surface 55 (not shown). Four circularly represented stimuli 25 are positioned on a straight frame 13 or associated lens or surface 55 at the base 95 of the cone 93 whereby the stimuli 25 project light 97, represented by the cones associated with each circularly represented stimulus 25, on the patient's first (R) eye 35 or second (L) eye 37. A cylinder 99 located between the patient's eyes 35, 37 represents the embodiment's contact point with the patient's nasion 77 (not shown). The plurality of lights or mechanical stimuli 25 may be placed anywhere on the frame 13 and/or lens or surface 55 as desired or required.

Gross visual field deficits may exist in one or more gross visual fields 75a, 75b, 75c, 75d as shown in FIG. 15. It should be appreciated that gross visual fields 75a, b, c, d are examples of gross visual fields tested in one embodiment and that other gross visual fields may be tested. It is suggested that the patient 19 follow up to receive comprehensive visual field testing following a positive screening test.

Figure 11A:
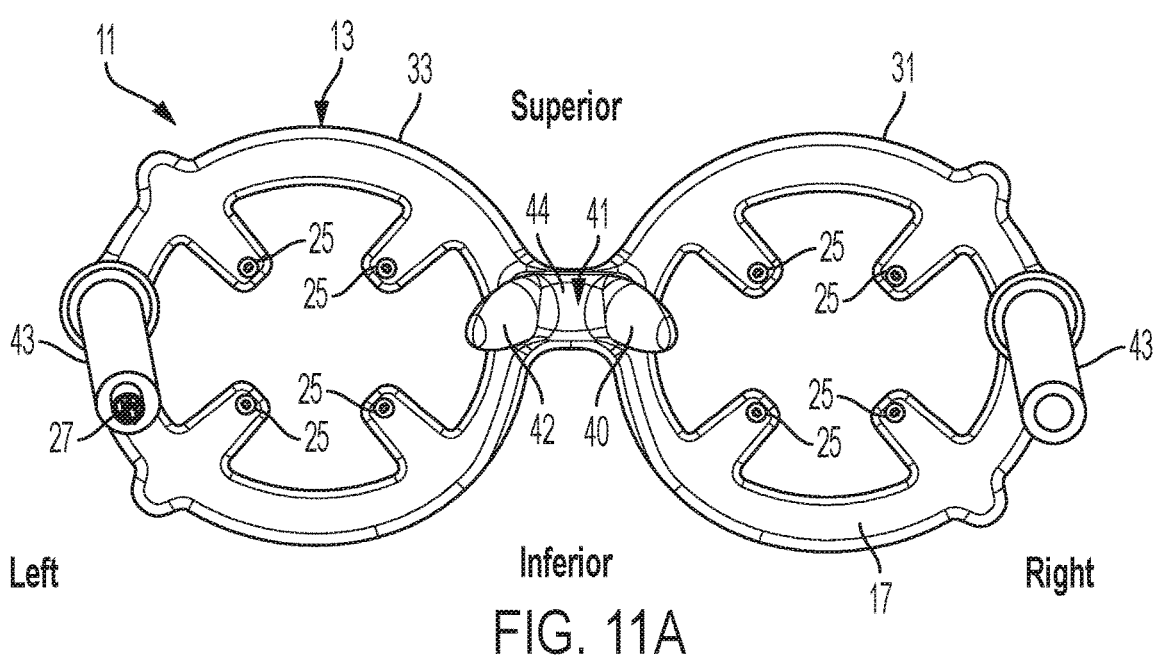
FIG. 11A is a schematic diagram illustrating the patient's perspective of one embodiment of the present invention.
Figure 11B:
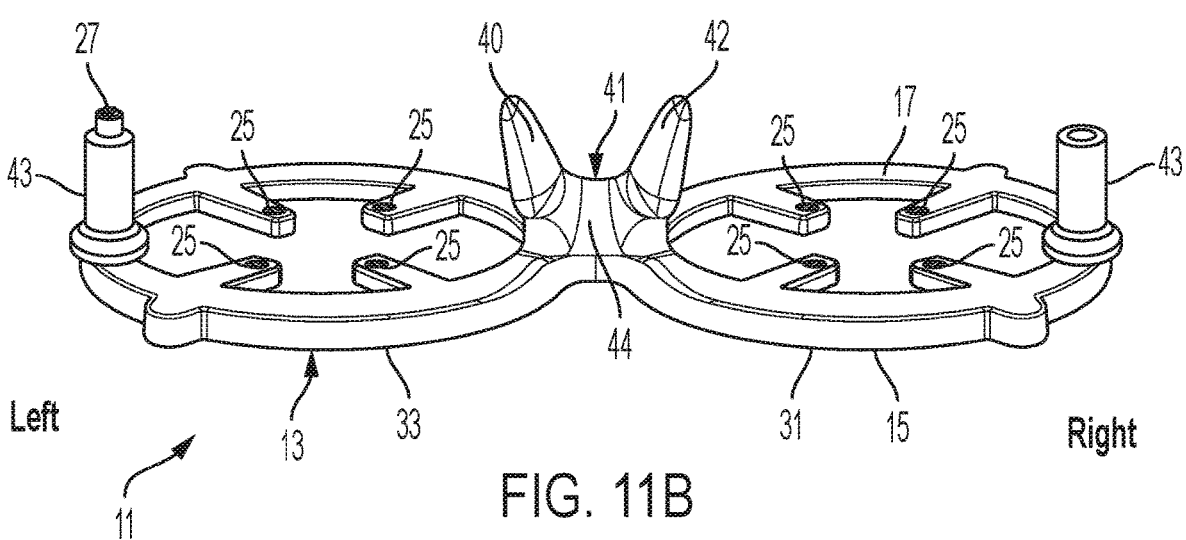
FIG. 11B is a schematic diagram illustrating an inferior perspective view of one embodiment of the present invention.
Figure 12:
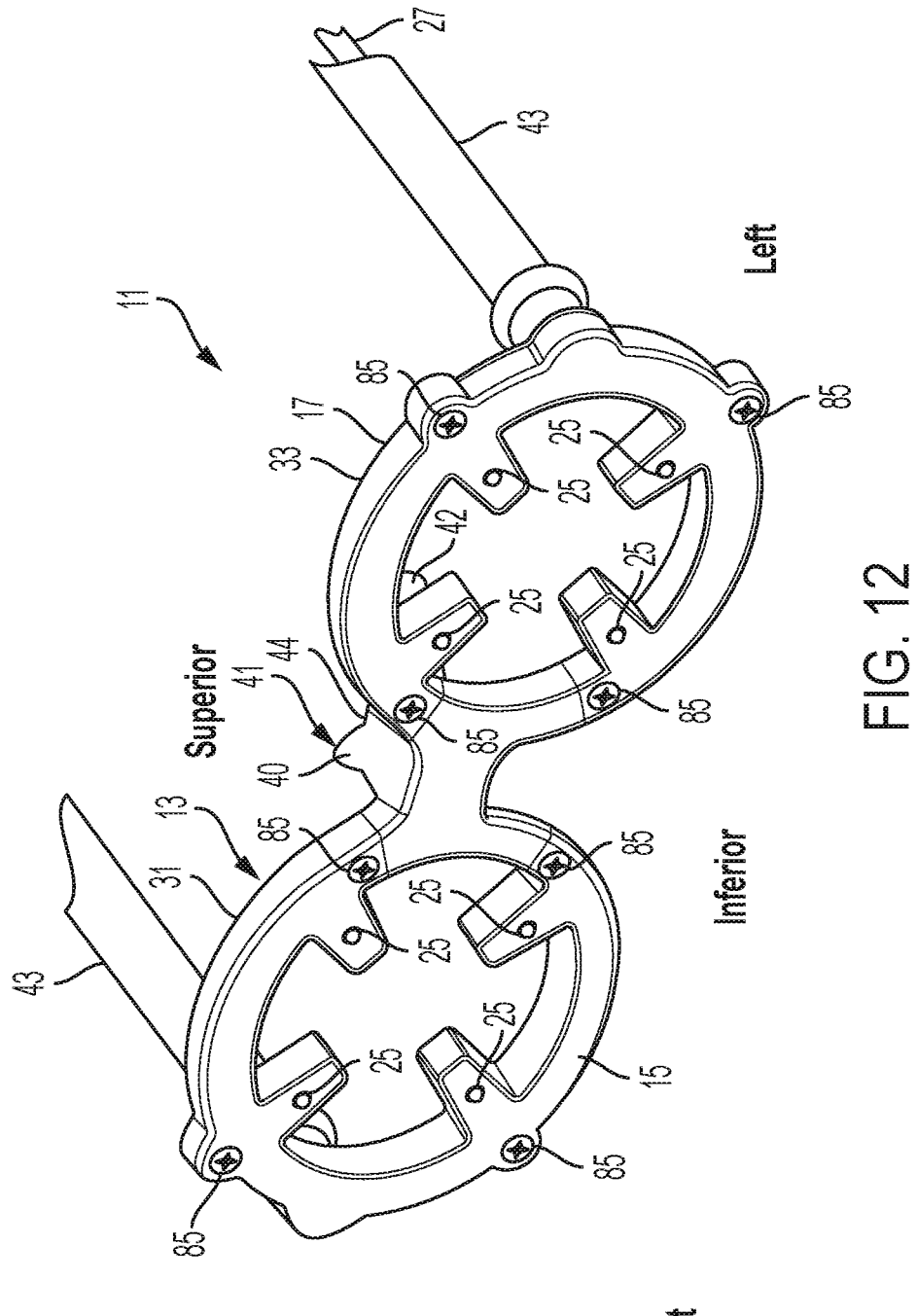
FIG. 12 is a schematic diagram illustrating an offset view (superior and frontal) of one embodiment of the present invention with visible LED stimuli.

The system 11 may be designed using a frame 13 that rests near the patient's eyes 35, 37, such as those used for goggles or glasses that may or may not contain lenses or surfaces 55 and may or may not be attached to the patient's face as shown in FIGS. 11A and B, 12, 13, and 14A and B. Attachment methods may include a stabilizer structure such as a strap 45, temples 43 such as those on glasses, or a nasion brace 41, or tape, glue, or some other sort of sticky material. In one embodiment, the frame is held together by screws 85 as shown in FIG. 12, but it should be appreciated that other embodiments may use other fastening means, adhesive means or require no fastening means.

Figure 18:
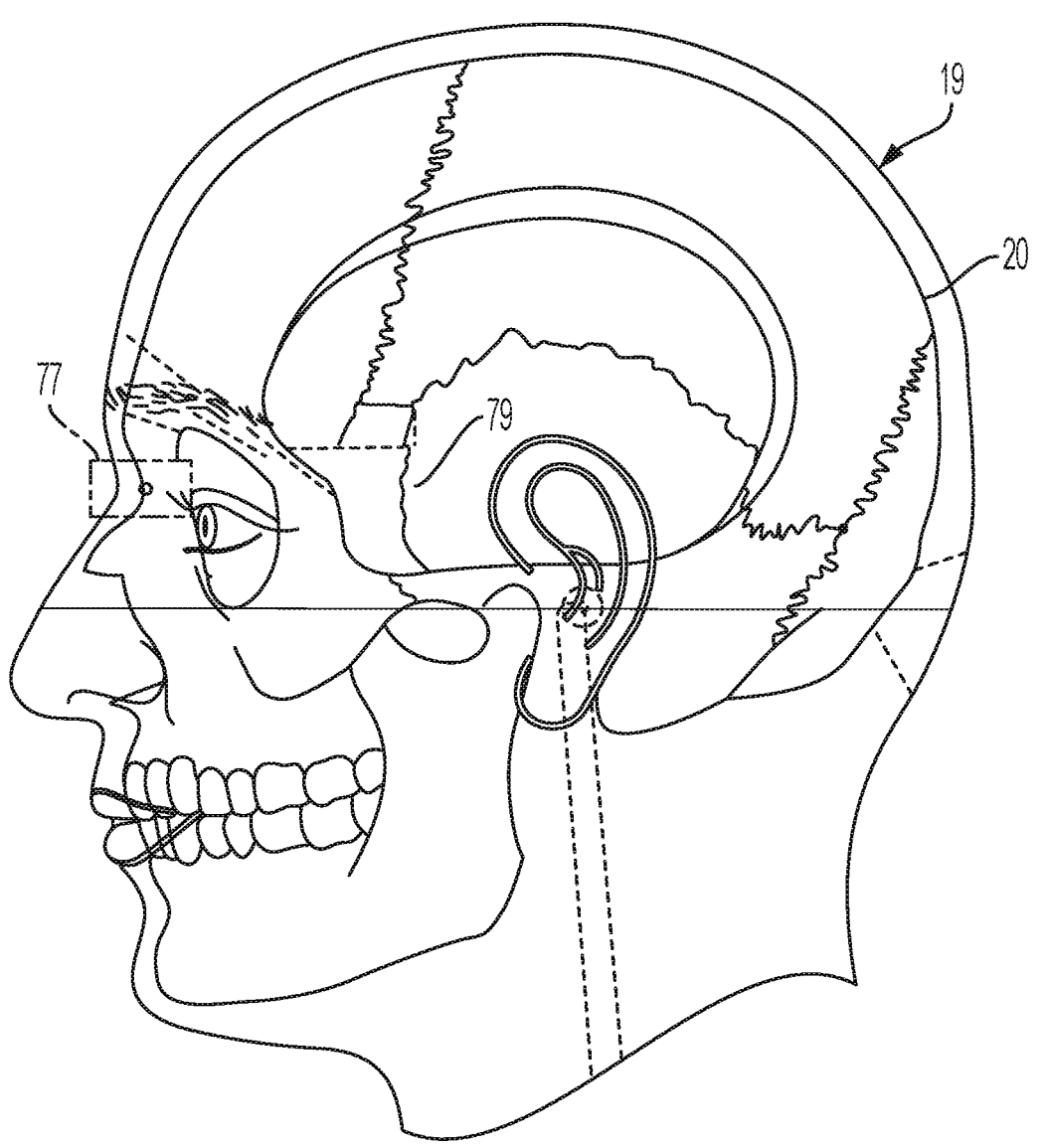
FIG. 18 is a schematic diagram illustrating an anatomical view of a patient's skull, nasion, and temple.
Figure 20:
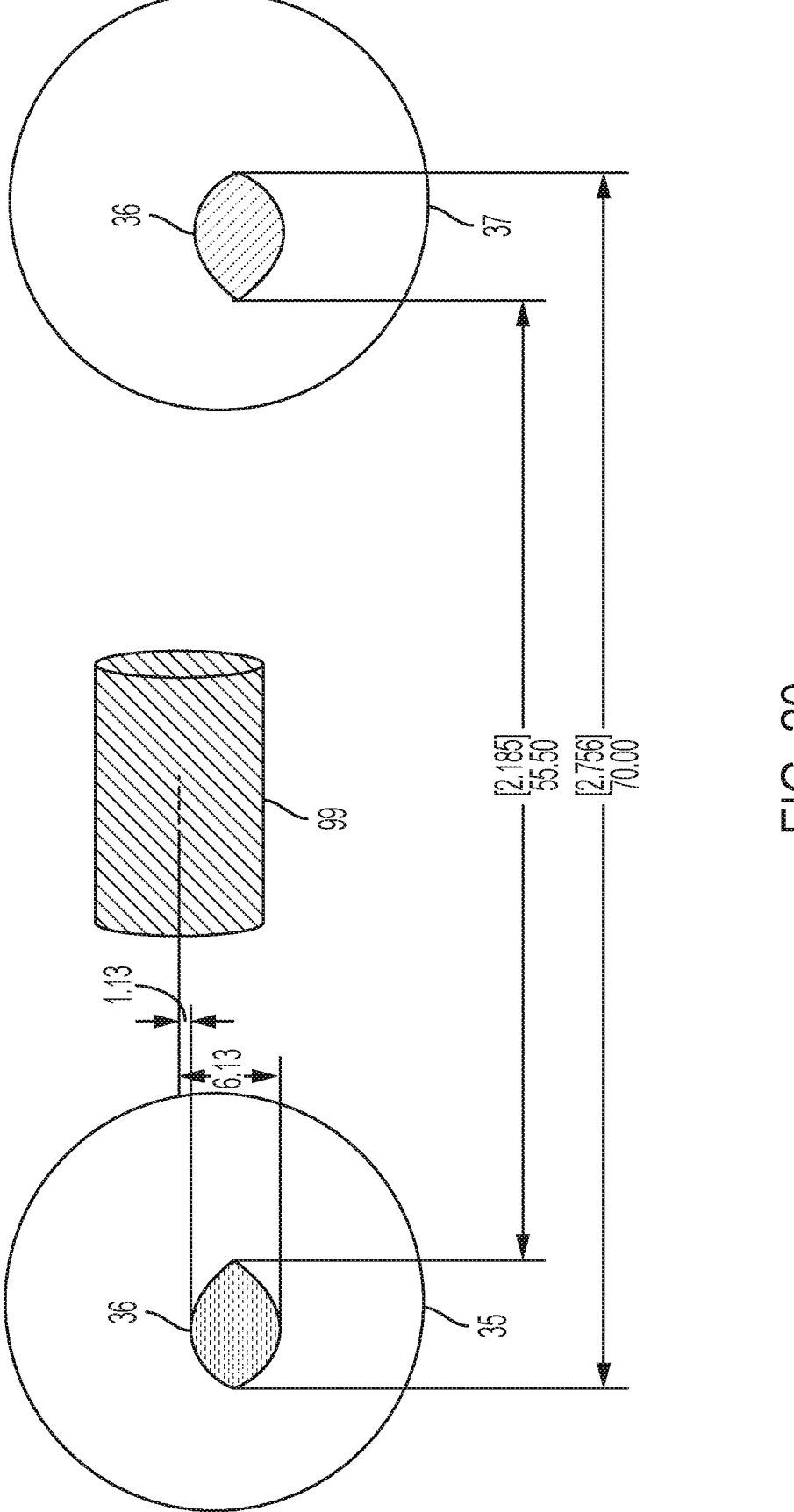
FIG. 20 is a schematic diagram illustrating the range in interpupillary distances (IPDs) between and vertical variation of the patient's eyes and pupils with respect to the nasion.

In one embodiment, as shown in FIGS. 11A and B, the attachment method is a nasion brace 41, having a right prong 40 and a left prong 42, that is located at the patient's nasion 77. The location of the nasion 77 is shown in relation to a patient 19, the patient's skull 20, and the patient's temple 79 in FIG. 18 and in relation to a patient's eyes 35, 37 and pupils 36 in FIG. 20 (for a specific embodiment). FIG. 20 provides the tolerances (as called out in illustration) that may be used with an embodiment for interpupillary distances (IPDs) and the vertical variation with respect to the nasion 77. Other tolerances may be implemented for other embodiments.

Figure 3:
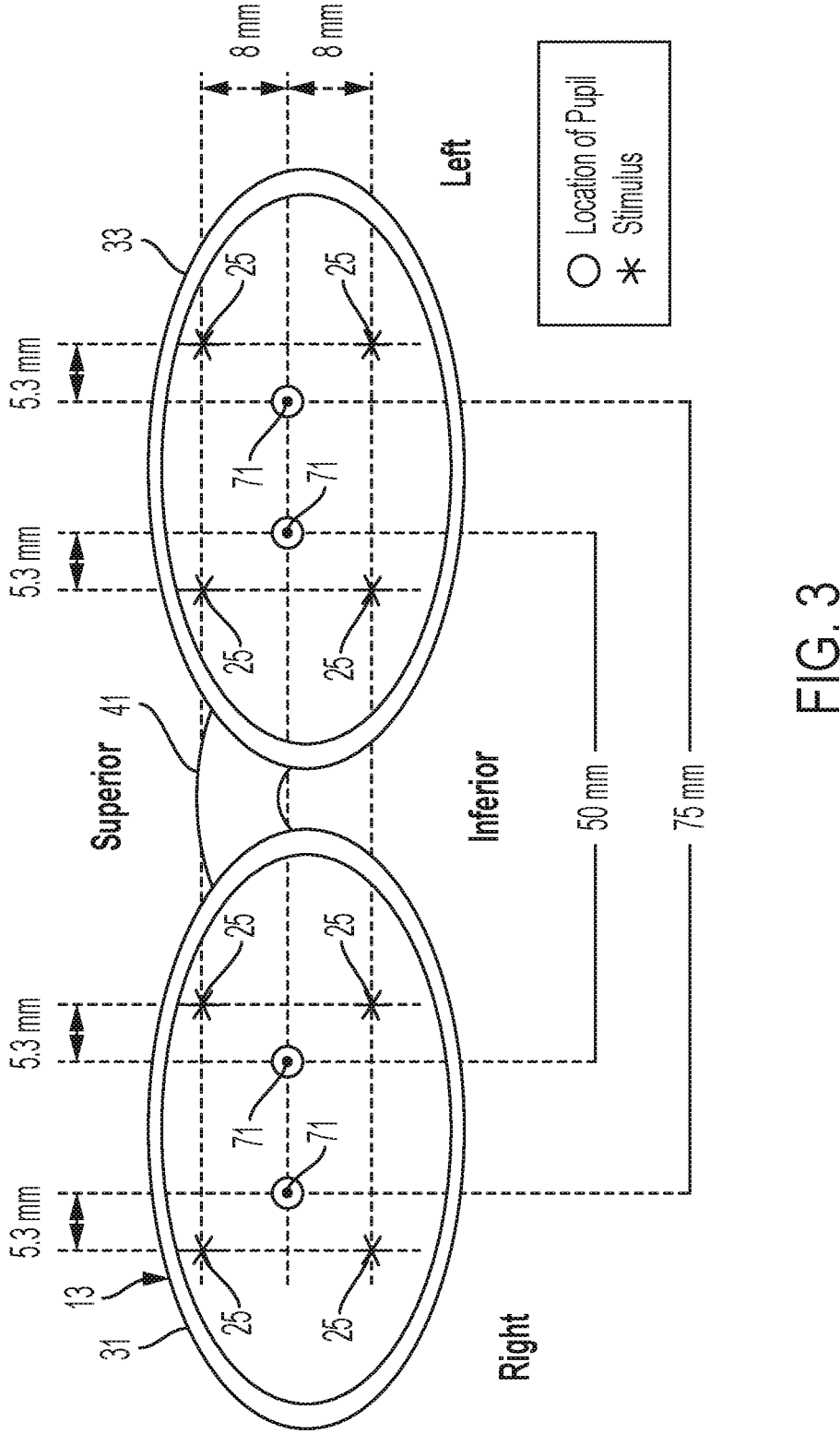
FIG. 3 is a schematic diagram illustrating a frontal view of relative locations of stimuli under the assumption of a vertex distance of 12 mm where positions are established based on a range of interpupillary distances (IPDs) of 50 and 75 mm.
Figure 9:
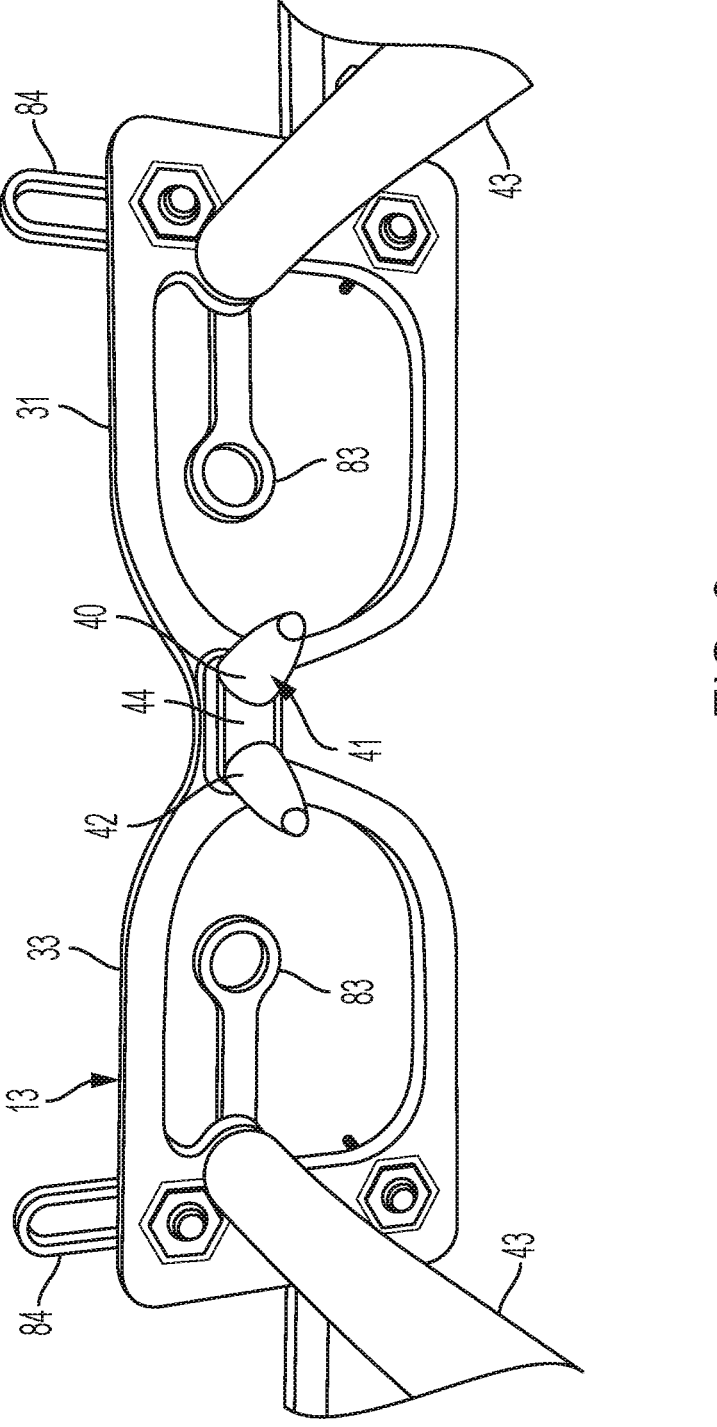
FIG. 9 is a schematic diagram illustrating one embodiment of the present invention with a pupil finder structure, nasion brace, and two temples of the frame.
Figure 13:
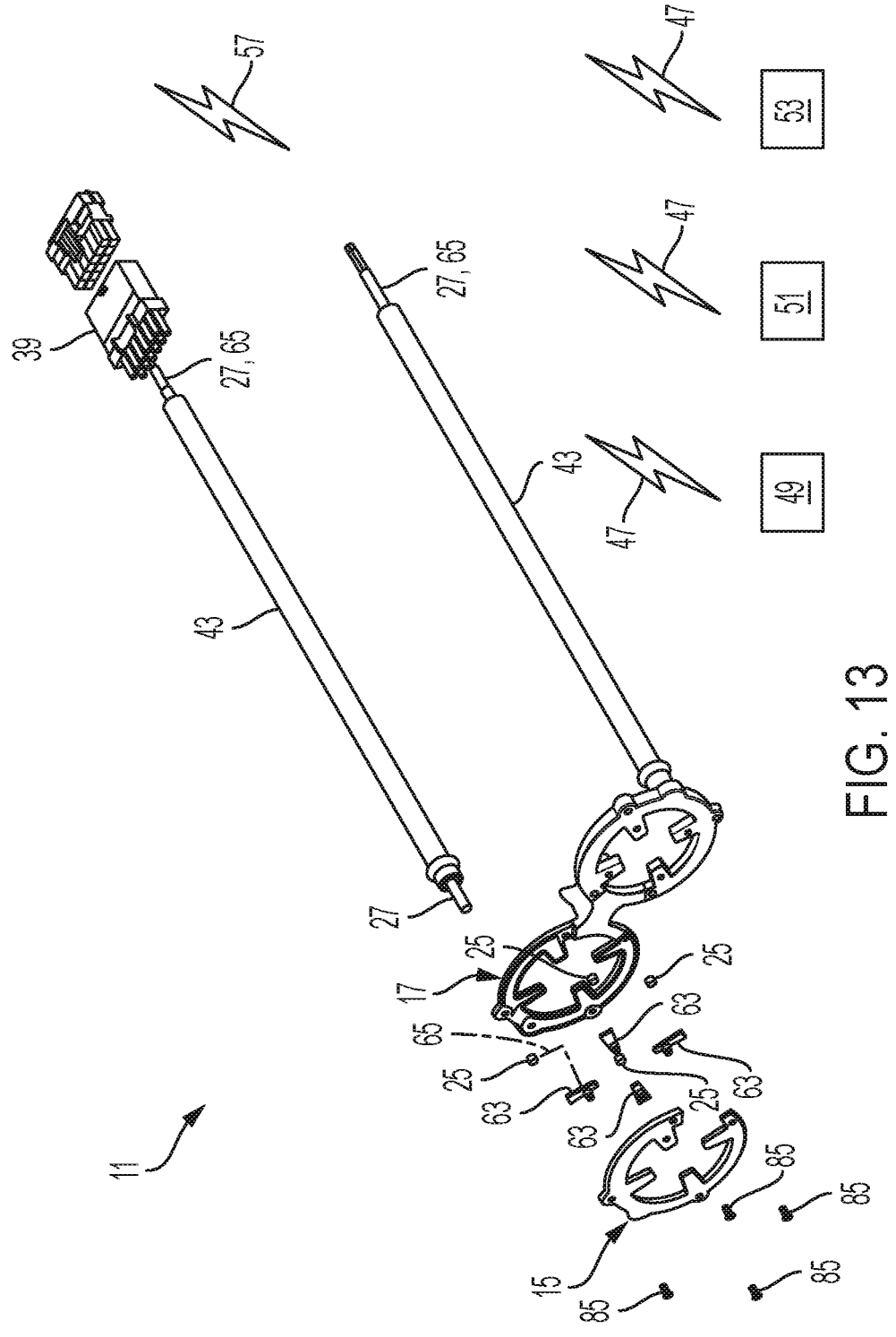
FIG. 13 is a schematic diagram illustrating an exploded view of the components of a portion of one embodiment of the present invention as well as an assembled view of the components of a portion of the embodiment including printed circuit boards, LEDs and a transmitter, receiver, and power source in wireless communication with one or more aspects of this embodiment of the present invention.
Figure 14A:
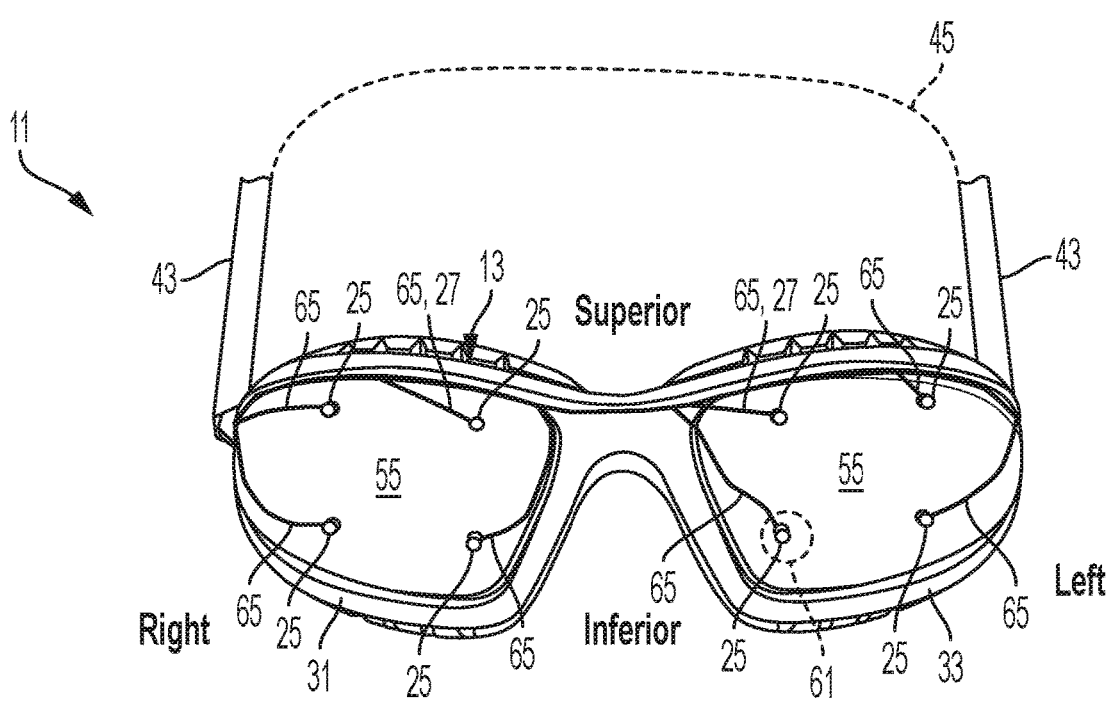
FIG. 14A is a schematic diagram illustrating one embodiment of the present invention with non-activated visual stimuli positioned on a lens or surface of the embodiment and one possible strap location.

Visual stimuli 25, in the form of single sources of light or mechanical stimulus, are mounted on, as shown in FIGS. 14A and B, or within, as shown in FIGS. 11A and B, a straight or curved frame 13 or associated lens or surface 55 such that they are able to be clearly seen from the front of the frame 15 and back of the frame 17 as shown in FIGS. 2A and 2B. In one embodiment, a visual barrier 81 blocks the patient's ability to see stimuli 25 positioned on the first side of the frame with the patient's second (L) eye 37 and stimuli 25 positioned on the second side of the frame with the patient's first (R) eye 35. The visual stimuli 25 are connected to a processor or controller 39 via hard wired communication 27 or wireless communication 47. In one embodiment, the hard wired communication 27 between the processor or controller 39 and the visual stimuli 25 extends within or along at least one temple 43 or horizontal stabilizer, as shown in FIGS. 11A, 12, and 13. In another embodiment, the wireless communication 47 between the visual stimuli 25 and the processor or controller 39 comprises a transmitter 49 and a receiver 51 or a transmitter 49 and receiver 51 configured to be in electrical communication with a power source 53, as shown in FIG. 13. In one embodiment, the power source 53 is configured to be in communication with the processor or controller 39. In another embodiment, the power source 53 is configured to be in communication with the visual stimuli. In another embodiment, the power source 53 is configured to be in communication with the processor or controller 39 and the visual stimuli 25. In some embodiments, the specified presentation order of the visual stimuli 25 is determined by the processor or controller 39 or an operator 21, or an operator 21 operating the processor or controller 39 before, during, or after executing one or more specified orders. In some embodiments, an operator 21 may repeat the activation of one or more visual stimuli 25 when the feedback provided by the patient 19 is unable to be observed by the operator 21. The visual stimuli 25 are located at a degree range 69 from a patient's pupil center 71 with interpupillary distances (IPDs) between 50 and 75 mm, which accounts for the vast majority of adults (FIGS. 2A and 2B; FIG. 3). The degree range 69 is a range of degrees nasally and temporally from a patient's pupil center 71 for patients 19 with interpupillary distances (IPDs) between and inclusive of about 50 and about 75 mm, and the visual stimuli 25 are positioned along a line 87 corresponding to the degree range 69 (FIG. 16). The stimuli 25 are also positioned along a line 87 corresponding to the degree range 69 from the central vision in the inferior and superior directions to account for variance in the vertical position of pupils 36 relative to the system 11 (FIG. 17). In one embodiment, a pupil finder structure 83 is in mechanical communication with the frame 13 and a slot or track 84 allowing the movement of the frame 13 or the pupil finder structure 83 to locate the patient's pupil center 71 as shown in FIG. 9. The position along a line 87 corresponding to the degree range 69 may rotate along the patient's pupil center 71 such that the position along a line 87 corresponding to the degree range 69 is located at any point around the 360 degree rotation about the pupil center 71.

In one embodiment, the degree range 69 is about 24 degrees as shown in FIGS. 2A, 2B, 16, and 17, although it should be appreciated that other degree ranges may be used in other embodiments, including: a range of about 23 degrees to about 25 degrees; a range of about 22 degrees to about 26 degrees; a range of about 18 degrees to about 30 degrees; a range of about 24 degrees to about 34 degrees; a range of about 0 degrees to about 30 degrees; a range of about 0 degrees to about 60 degrees, or a range of about 0 degrees to about 90 degrees. In an embodiment, the degree ranges may be less than or greater than the ranges provided.

Referring to FIGS. 2A-2B, in an embodiment, the patient's interpupillary distance (IPD) may be a variety of distances depending on the size of the patient 19. For example in an embodiment, of which should not be construed as limiting, the patient's interpupillary distance (IPD) may be in the range of 50 mm and 75 mm (as shown in FIGS. 2A-2B). In an embodiment the interpupillary distance (IPD) may be less than 50 mm or greater than 75 mm depending on the size of the patient 19.

In another embodiment, the processor or controller 39 is included in a kit configured to be used with the system 11.

Figure 10:
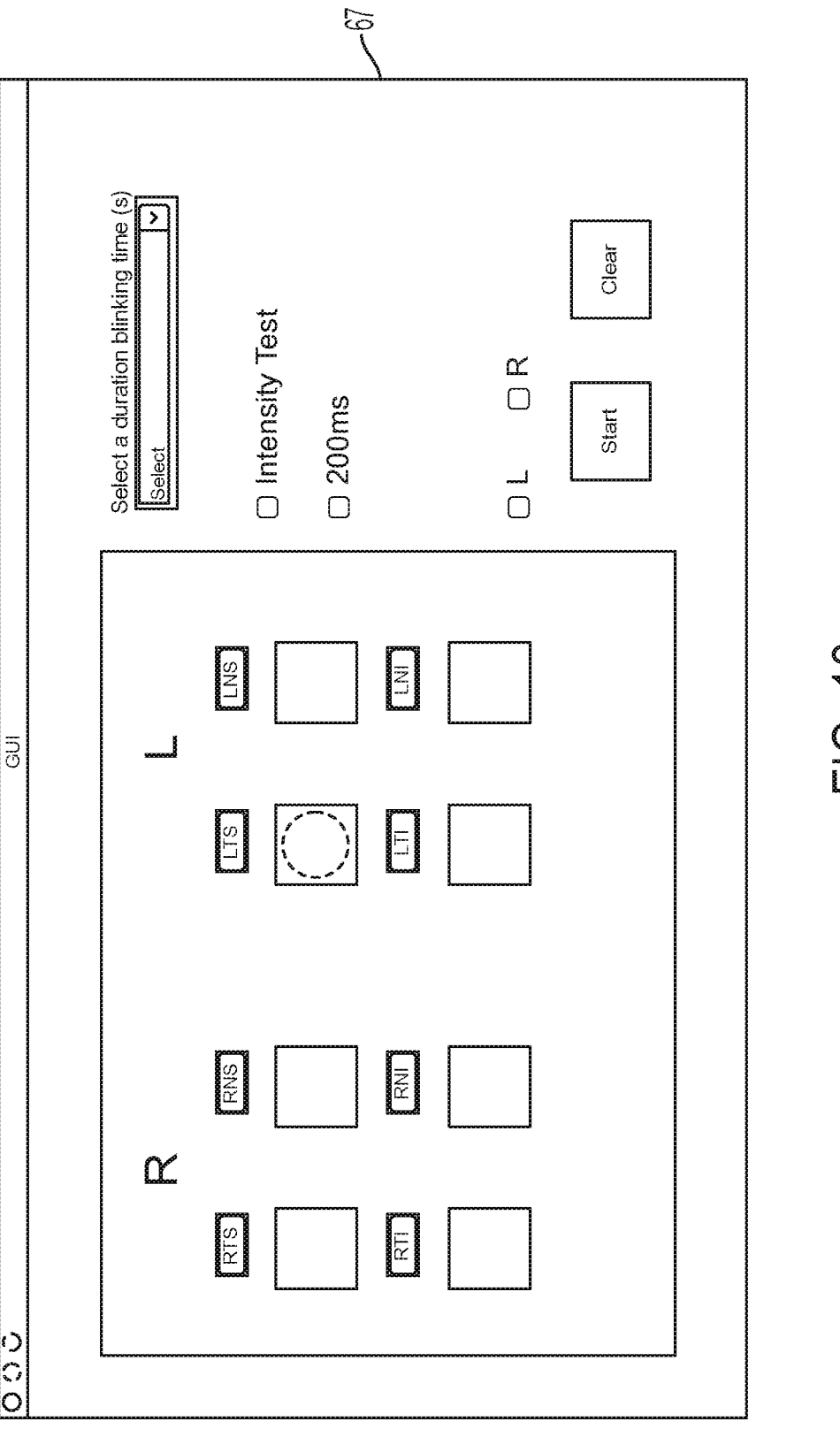
FIG. 10 is a schematic diagram illustrating an example of a graphical user interface used in conjunction with one or more aspects of embodiments of the present invention.

The presentation of the visual stimuli 25 is controlled by the visual stimuli 25 or a processor or controller 39 such that the stimuli 25 are presented randomly, both in order and in duration, between trials. Each stimulus 25 may also be controlled manually via computer interface 67, an example of which is shown as FIG. 10. The processor or controller 39 may be powered by a power source 53, either external to the system 11 or embedded within the system 11. The system 11, processor or controller 39, and computer interface 67 may interface through various means, either through hard wired communication 27 or wireless communication 47.

It should be appreciated that in some embodiments the processor or controller 39 may also be a microcontroller, a servomotor, a computer, or a circuit board 63, or a processor or controller or controller 39 and a microcontroller, and/or a computer, and/or a circuit board 63 where the processor or controller 39 controls the microcontroller or servomotor, and/or a computer, and/or a circuit board 63 and the microcontroller or servomotor, and/or computer, and/or circuit board 63 control the visual stimuli 25.

Each light 25 is designed as a separate circuit containing a LED light, fiber optic light, pinpoint-type light, or small target light and a resistor of a resistance that makes the light 25 sufficiently bright for easy visualization.

Figure 14B:
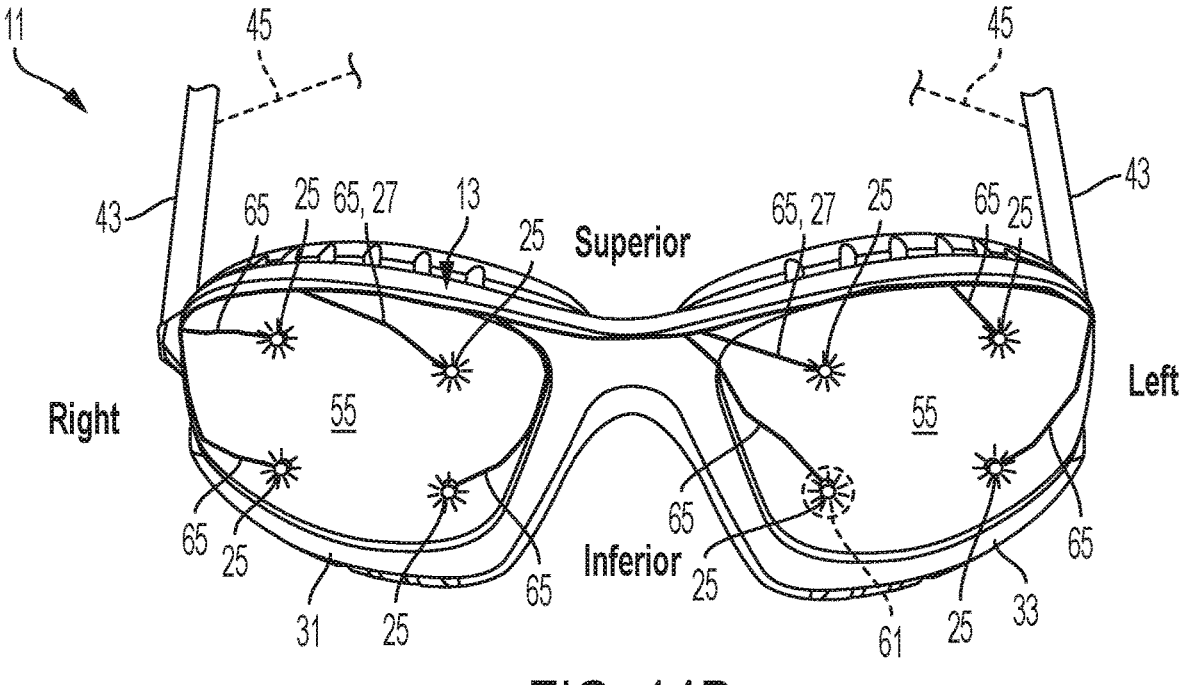
FIG. 14B is a schematic diagram illustrating one embodiment of the present invention with activated visual stimuli positioned on a lens or surface of the embodiment and another possible strap location.

In one embodiment, each light or mechanical stimuli 25 also includes an adjacent material 61 that is light-absorbent, unreflective, less-reflective, anti-reflective, or has a low reflexive index (FIGS. 14A and 14B).

Figure 4:
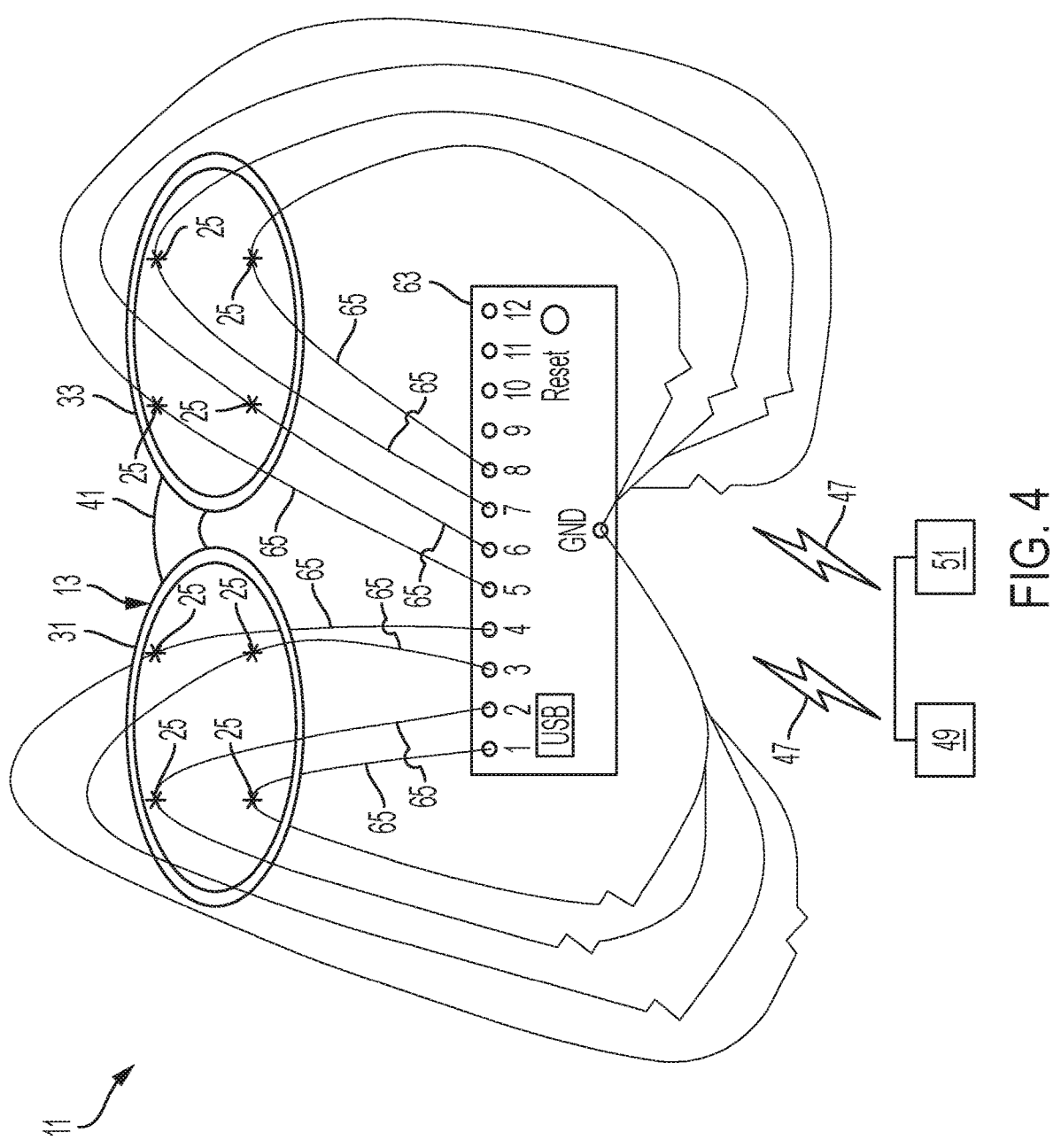
FIG. 4 is a schematic diagram illustrating a schematic of circuit board layout and design where the resistance of each circuit is dependent on the light used and the device is powered using direct current through a USB connection and a transmitter and receiver in wireless communication with one or more aspects of this embodiment of the present invention.

In an embodiment, each light or mechanical stimulus 25 is connected by hard-wired or wireless communication, so as to define circuit board hard-wired or wireless communication 65, between a circuit board 63 and a light or mechanical stimuli 25 (FIG. 4). In another embodiment, the circuit board wireless communication 65 comprises a transmitter 49 and a receiver 51. In an embodiment, the system may include both lights and mechanical stimuli.

In an embodiment, at least one light 25 contains a resistor of a resistance that makes the light 25 sufficiently bright to induce a dilation or constriction reaction from at least one of the patient's pupils 36 or to assess the reaction or inaction or no movement of the patient's pupils 36 where one or more operators 21 is capable of observing the reaction.

Figure 5:
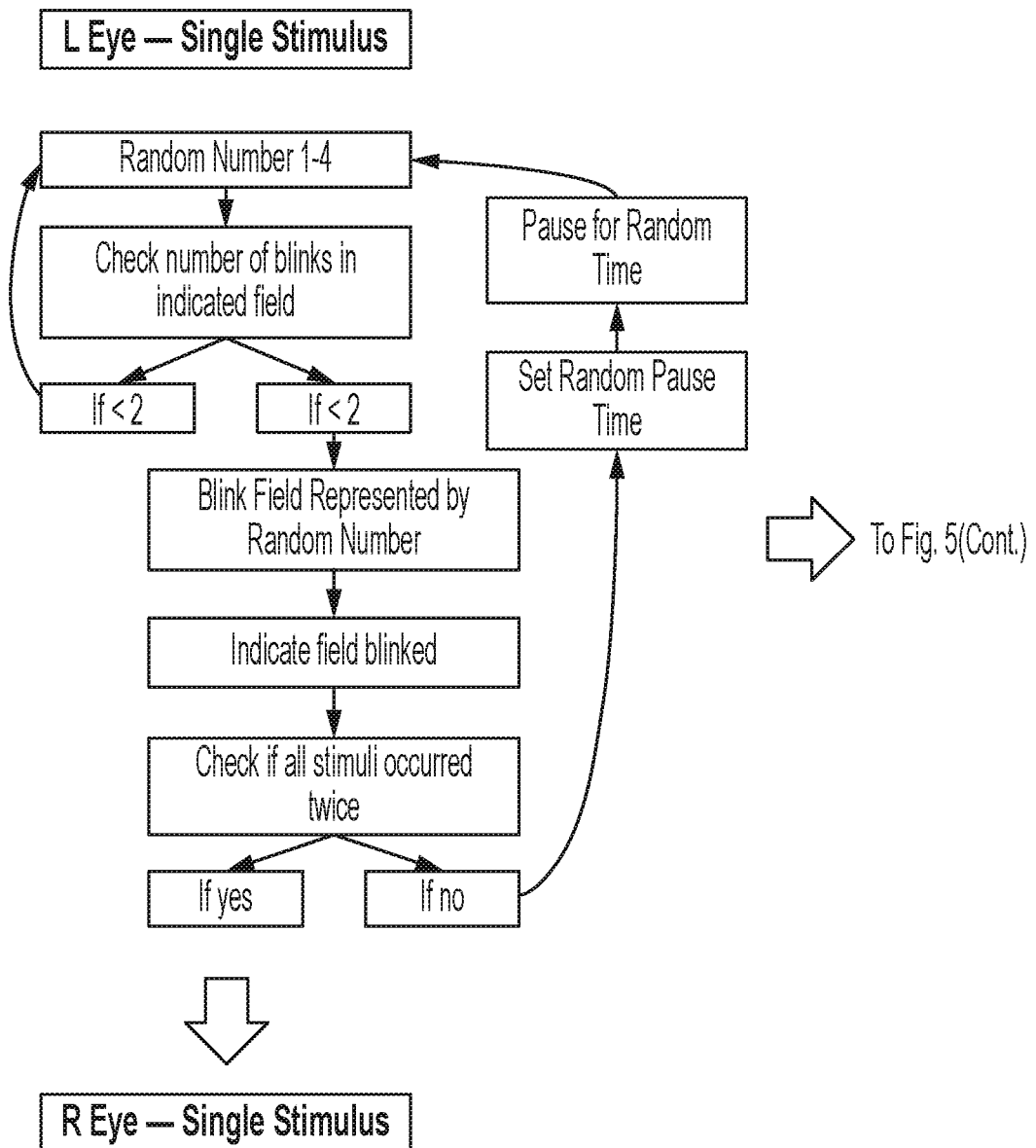
FIG. 5 is a flowchart illustrating an overview of an algorithm allowing for random order of stimuli presentation and for random duration between stimuli presented in both single stimulus and multiple stimulus trials.
Figure 5:
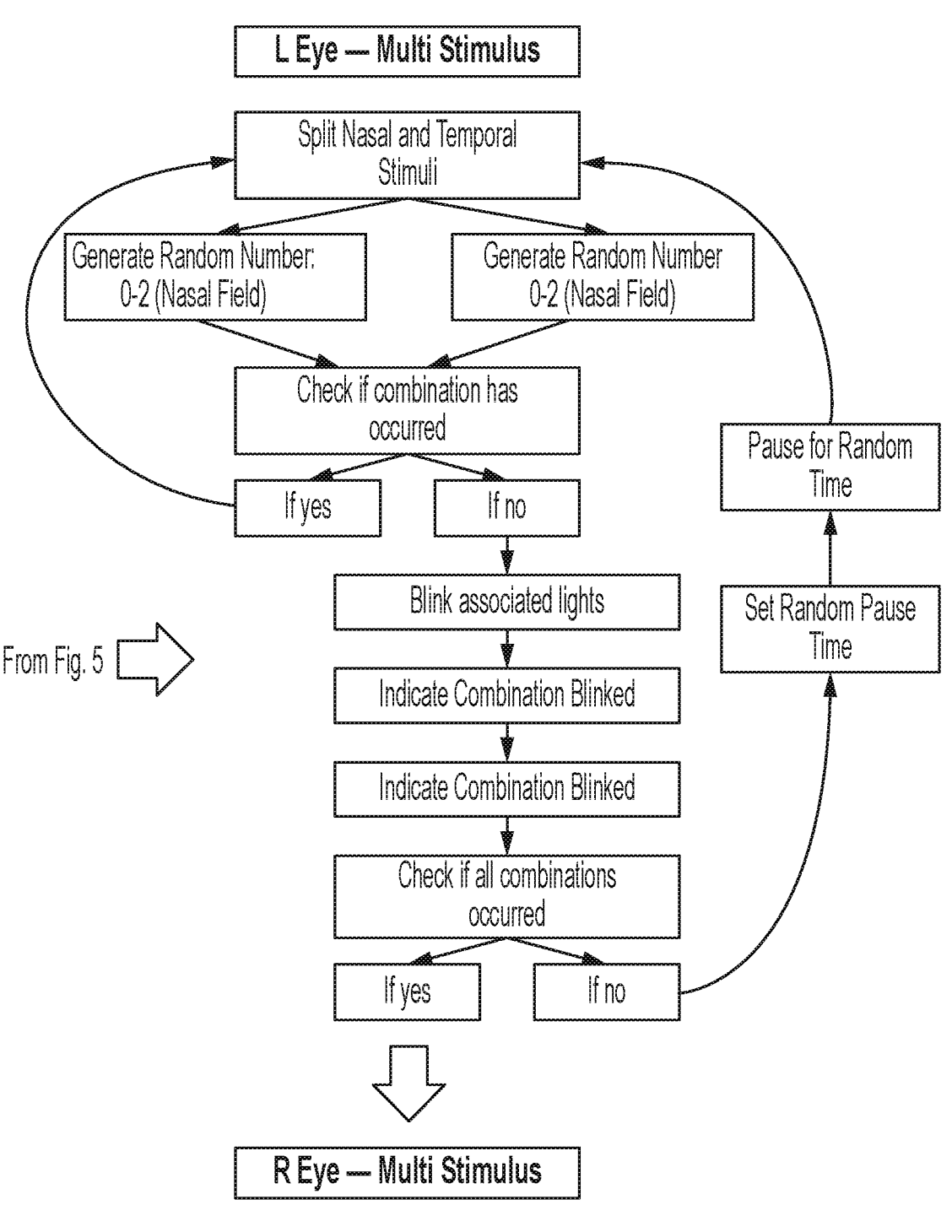
Figure 6:
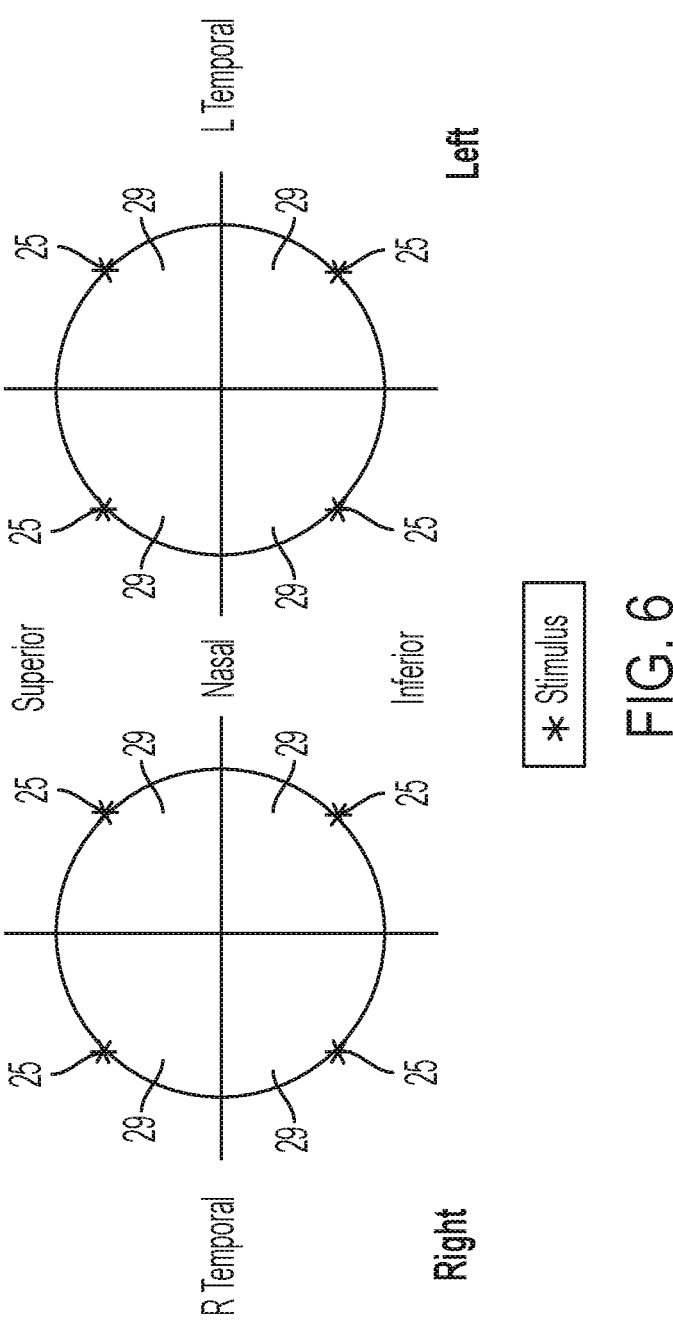
FIG. 6 is a schematic diagram illustrating an overview of defined visual field quadrants in each eye where naming would combine the two descriptors of each quadrant (e.g. L Temporal Superior).

During each trial, either one or two stimuli 25 will be presented (flash or other stimuli) simultaneously. The algorithm (and technique and process), as depicted in FIG. 5, will begin by presenting, in random order at random intervals, stimuli 25 in each of the four defined quadrants 29 of the second (L) eye 37 (FIG. 6) on the second side of the frame 33. It should be appreciated that the specified presentation order may also include presenting one or more stimuli randomly, sequentially, serially, repeatedly, or in any combination of lights (or mechanical stimuli) or orders. The patient 19 will indicate, verbally or as otherwise determined, when they see a stimulus 25. The integrity of the test is preserved by the changes in time between successive trials. The operator 21 is also responsible for ensuring that the patient's gaze is focused directly ahead during each trial. In an embodiment, the system may include both a plurality of lights and mechanical stimuli.

An invalid trial results from an indication that the patient 19 saw a stimulus 25 that was not present, that a patient's gaze wandered away from midline, or any other indication that the trial cannot be considered valid. A valid trial is one that is not invalid in which it can be reasonably determined that the patient 19 either accurately indicates a stimulus 25 was present or fails to indicate that a stimulus 25 was seen. A successful trial is defined as a valid trial in which the patient 19 successfully indicates that they saw the stimulus 25. A failed trial is defined as a valid trial in which the patient 19 fails to indicate that a stimulus 25 was presented. A likely visual field deficit can be implied by the presence of one or more quadrants 29 with at least one failed trial. It should be appreciated that testing to allow for more than one failed trial increases the accuracy of the results and may be preferred, although at times just one failed trial will be sufficient for a result.

The algorithm (and technique and process) will next present, in random order at random intervals, stimuli 25 in each of the four defined quadrants 29 of the first (R) cye 35 (FIG. 6) on the first side of the frame 31. Procedures and outcomes are defined in the same way as with the second (L) eye 37. To determine neurologic deficits, results between eyes 35, 37 should be correlated.

In one embodiment, one or more operators 21 may determine a patient's score that may be: '0' where there is a valid trial and where the feedback provided by the patient 19 indicates that no activated lights were missed; '1' where the feedback provided by the patient 19 indicates quadrantanopsia or partial quadrantanopsia; '2' where the feedback provided by the patient 19 indicates hemianopsia; or '3' where the feedback provided by the patient 19 indicates peripheral blindness as shown in FIG. 1. It should be appreciated that although FIG. 1 shows quadrantanopsia or partial quadrantanopsia and hemianopsia as located on the right side of the first (R) eye 35 and the second (L) eye 37, the location may also be on the left side of the first (R) eye 35 and the second (L) eye 37 or on the left or right side of one of both eyes 35, 37.

In another embodiment, the patient's condition may be determined to be: without deficiency of detecting all quadrants of one or both eyes 35, 37; deficient in one quadrant of one or both eyes 35, 37; deficient in two quadrants or one or both cyes 35, 37; or deficient in four quadrants or one or both eyes 35, 37.

Figure 7:
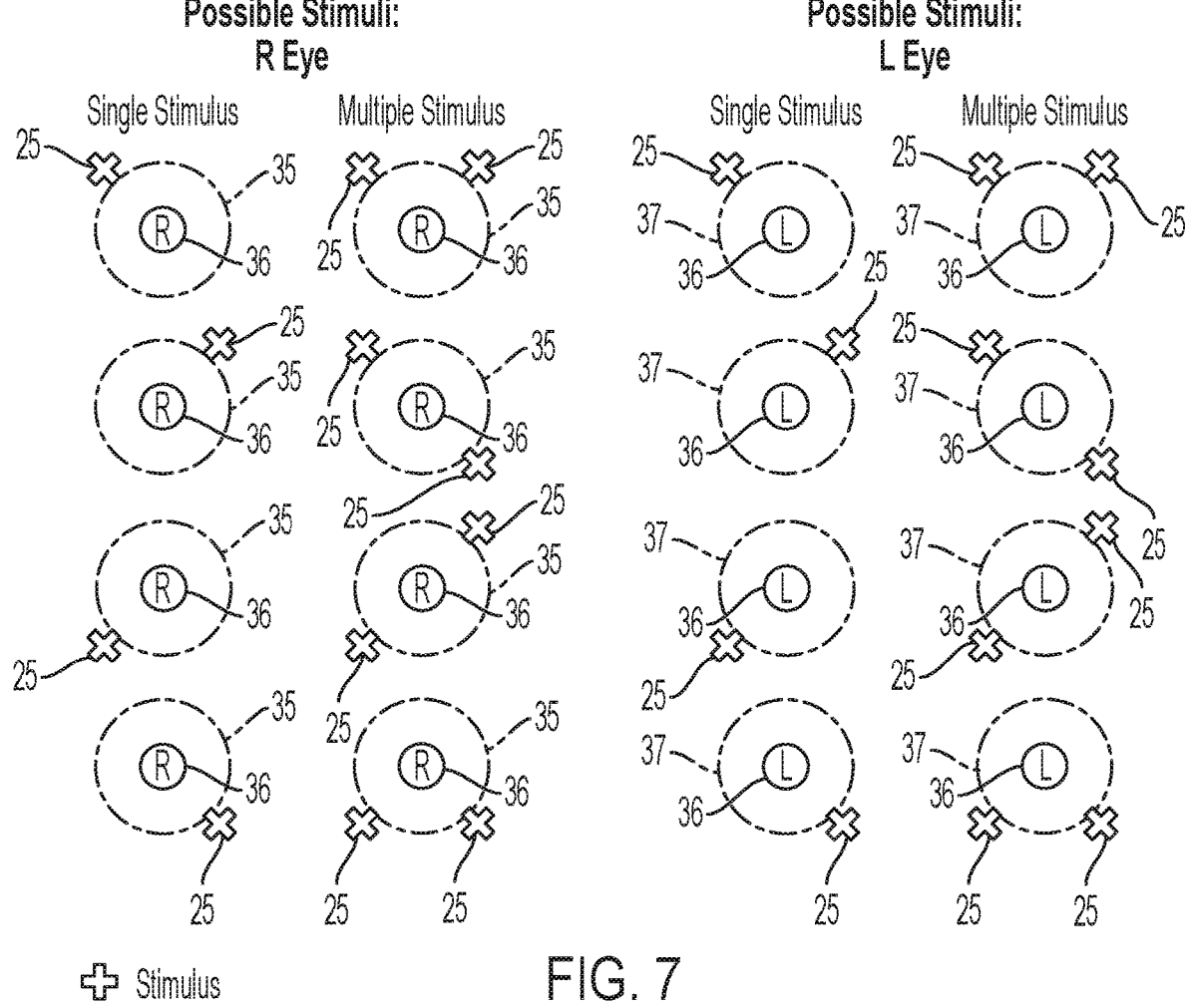
FIG. 7 is a schematic diagram illustrating the possible locations of stimuli for both the R and L eyes during a multiple stimulus testing phase.

After the first two phases of the exam, the operator 21 may proceed to the second phase of testing if the patient 19 is able to differentiate between seeing one or two stimuli 25 and to test for extinction. The second phase presents either one or two stimuli 25 and the patient 19 reports the number of stimuli 25 seen. Each eye 35, 37 will be individually tested, starting with the L eye 37. The operator 21 will explain to the patient 19 that they now need to indicate that either one or two lights or mechanical stimuli 25 were seen. One of 8 outcomes, as depicted in FIG. 7, will randomly occur separated by random time intervals. The trials with two stimuli 25 present will always contain a stimulus from the nasal and temporal fields in order to test for extinction.

If a connection between a processor or mechanical stimuli 39 and computer interface 67 is enabled, the operator 21, through the use of pre-determined commands, can assume manual control of the order of stimuli 25 and time between stimuli 25 presentation. This connection may occur through hard wired communication 27, use of web-based application, connection through video conferencing provider, or some other form of wireless communication 47, hard wired communication 27, or remote communication 57 between the remotely located operator 21 and the system 11 as shown in FIG. 13.

In one embodiment, one or more feedback capturing devices 59, including but not limited to a video recorder, an image capturing device or camera, or an image capturing device or camera with a microphone, are positioned at the vantage point 23 to directly observe the patient's one or both eyes 35, 37. In one embodiment, the one or more feedback capturing devices 59 are in remote communication 57 with one or more operators 21 located remotely. In one embodiment, the remote communication 57 includes decryption and/or encryption. In one embodiment, the one or more feedback capturing devices 59 and one or more operators 21 are positioned at the vantage point to directly observe the patient's one or both eyes 35, 37.

The primary use case identified for the system 11 is for telestroke consults. Use is not limited to stroke or telemedicine consults, however, but should provide a standardized system 11 for rapid screening for visual field deficits.

It should be appreciated that although the VRAD is used to execute the methods disclosed herein, in another embodiment a different device may be used to execute the same methods.

Figure 8:
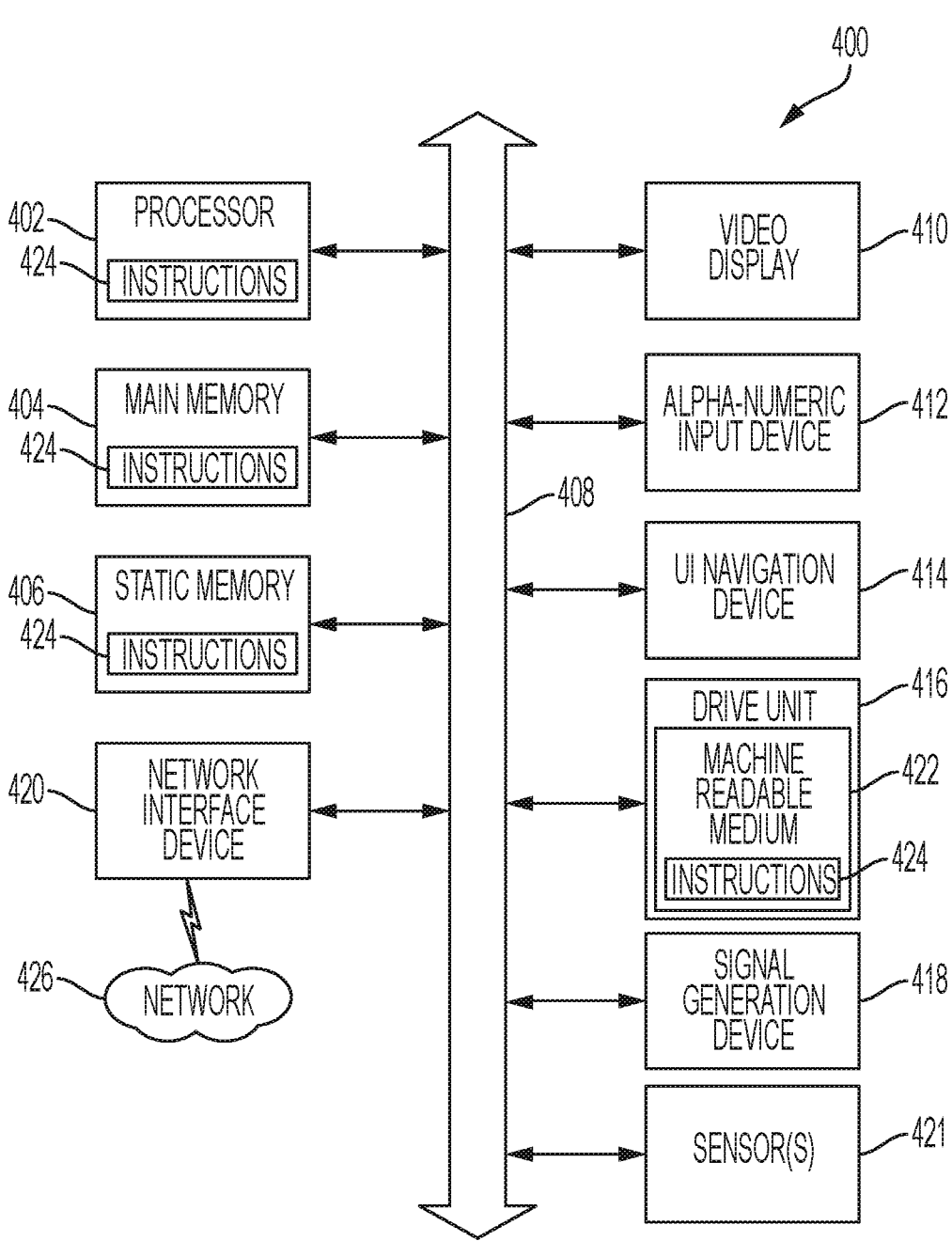
FIG. 8 is a block diagram illustrating an example of a machine upon which one or more aspects of embodiments of the present invention can be implemented.

FIG. 8 is a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors or controller that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs)).

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a stand-alone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit 410, input device 417 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/operator/customer/client or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the environmental, anatomical, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

It must also be noted that, as used in the specification and the appended claims, the singular forms "a." "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, or method steps, even if the other such compounds, material, particles, or method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the nth reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

EXAMPLES

Practice of an aspect of an embodiment (or embodiments) of the invention will be still more fully understood from the following examples and experimental results, which are presented herein for illustration only and should not be construed as limiting the invention in any way.

Example 1. A system for performing rapid, interactive screening of visual fields of a patient, comprising:

a frame having a front and a back, wherein said back of said frame directionally faces a patient and said front of said frame is opposite said back of said frame and directionally faces one or more operators;

said frame configured to allow a vantage point adjacent to and in front of said front of said frame to allow direct observation of one or both eyes of said patient;

a plurality of lights or mechanical stimuli in mechanical communication with said frame, wherein upon activation of said plurality of lights or said mechanical stimuli, said plurality of lights or said mechanical stimuli are directly visible by said patient and said one or more operators, and wherein said plurality of lights or said mechanical stimuli are disposed in a position, wherein said position allows for the testing of a patient's visual fields; and said plurality of lights or said mechanical stimuli are configured to be in hard-wired or wireless communication with a processor or controller and said plurality of lights or said mechanical stimuli are configured to activate in a specified order, wherein said specified order is in accordance with a testing protocol.

Example 2. The system of example 1, wherein said specified order of activating said plurality of lights or said mechanical stimuli may include any one or more of the following: randomly, sequentially, serially, repeatedly, or in combination of said plurality of lights or mechanical stimuli.

Example 3. The system of example 1 (as well as subject matter in whole or in part of example 2), wherein said specified order includes:

either one or two of said plurality of lights or said mechanical stimuli are configured to activate simultaneously during said screening, and said plurality of lights or said mechanical stimuli are placed in communication with said frame in four quadrants that coincide with four quadrants of said patient's vision and are programmed such that each said quadrant of vision is tested at least once, in random order and/or at random intervals.

Example 4. The system of example 1 (as well as subject matter of one or more of any combination of examples 2-3, in whole or in part), wherein said specified order of activating said plurality of lights or said mechanical stimuli is configured to activate on a first side of said frame in relation to one of said eyes or on a first side and a second side of said frame wherein each of said first and second sides of said frame correspond respectively with a first said eye and a second said eye.

Example 5. The system of example 1 (as well as subject matter of one or more of any combination of examples 2-4, in whole or in part), further comprising a kit, wherein said kit comprises:

said processor or controller configured so as to be able to be in electrical communication with said plurality of lights or said mechanical stimuli, wherein said processor or controller is configured so as to be able to control said activation of said plurality of lights or said mechanical stimuli in the specified order, wherein said specified order is in accordance with said testing protocol.

Example 6. The system of example 1 (as well as subject matter of one or more of any combination of examples 2-5, in whole or in part), further comprising:

said processor or controller in electrical communication with said plurality of lights or said mechanical stimuli, wherein said processor or controller is configured to control said activation of said plurality of lights or said mechanical stimuli in said specified order, wherein said specified order is in accordance with said testing protocol.

Example 7. The system of example 1 (as well as subject matter of one or more of any combination of examples 2-6, in whole or in part), wherein said processor comprises a microcontroller.

Example 8. The system of example 1 (as well as subject matter of one or more of any combination of examples 2-7, in whole or in part), wherein said controller is a servomotor.

Example 9. The system of example 1 (as well as subject matter of one or more of any combination of examples 2-8, in whole or in part), further comprising at least one stabilizer structure in mechanical communication with said frame.

Example 10. The system of example 9, wherein said at least one stabilizer structure comprises a vertical stabilizer and/or a horizontal stabilizer.

Example 11. The system of example 9 (as well as subject matter in whole or in part of example 10), wherein said at least one stabilizer structure comprises at least one or more of any one of the following: a nasion brace, one or two temples, or at least one strap.

Example 12. The system of example 1 (as well as subject matter of one or more of any combination of examples 2-11, in whole or in part), wherein said hard-wired communication between said plurality of lights or said mechanical stimuli and said processor or controller extends within or along at least one temple.

Example 13. The system of example 1 (as well as subject matter of one or more of any combination of examples 2-12, in whole or in part), wherein said wireless communication between said plurality of lights or said mechanical stimuli and said processor or controller comprises a transmitter and a receiver.

Example 14. The system of example 13, wherein said transmitter and/or said receiver are configured to be in electrical communication with a power source.

Example 15. The system of example 1 (as well as subject matter of one or more of any combination of examples 2-14, in whole or in part), wherein said plurality of lights or said mechanical stimuli are disposed on said frame.

Example 16. The system of example 1 (as well as subject matter of one or more of any combination of examples 2-15, in whole or in part), further comprising: a lens disposed within said frame, wherein said plurality of lights or said mechanical stimuli are disposed on or within said lens.

Example 17. The system of example 1 (as well as subject matter of one or more of any combination of examples 2-16, in whole or in part), wherein said system is configured to allow remote communication for one or more operators to communicate with said patient.

Example 18. The system of example 1 (as well as subject matter of one or more of any combination of examples 2-17, in whole or in part), wherein said vantage point allows one or more operators, in front of said front of said frame, to directly observe one or both of the eyes of said patient.

Example 19. The system of example 18, wherein said vantage point allows one or more feedback capturing devices, positioned in front of and facing said front of said frame, to directly observe one or both of the eyes of said patient.

Example 20. The system of example 19, wherein said one or more feedback capturing devices is in remote communication with a remote system or with said one or more operators located remotely.

Example 21. The system according to example 20, wherein said remote communication includes decryption and/or encryption.

Example 22. The system of example 19 (as well as subject matter of one or more of any combination of examples 2-18 and 20-21, in whole or in part), wherein said feedback capturing device is a video recorder, an image capturing device or camera, or an image capturing device or camera with a microphone.

Example 23. The system of example 1 (as well as subject matter of one or more of any combination of examples 2-22, in whole or in part), wherein said vantage point allows one or more image feedback capturing devices, in front of said front of said frame, to directly observe one or both of the eyes of said patient.

Example 24. The system of example 23, wherein said one or more feedback capturing devices is in remote communication with a remote system or with said one or more operators located remotely.

Example 25. The system of example 24, wherein said feedback capturing device is a video recorder, an image capturing device or camera, or an image capturing device or camera with a microphone.

Example 26. The system of example 1 (as well as subject matter of one or more of any combination of examples 2-25, in whole or in part), further comprising a power source configured to be in communication with said processor or controller and/or said plurality of lights or said mechanical stimuli.

Example 27. The system of example 1 (as well as subject matter of one or more of any combination of examples 2-26, in whole or in part), wherein said plurality of lights include any one or more of the following: LED light, fiber optic light, pinpoint-type light, or small target light.

Example 28. The system of example 1 (as well as subject matter of one or more of any combination of examples 2-27, in whole or in part), wherein said plurality of said mechanical stimuli include any one or more of the following: mechanical device configured to provide a black and white target, color target, sign, symbol, figurine, bust, sculpture, or a picture.

Example 29. The system according to example 1 (as well as subject matter of one or more of any combination of examples 2-28, in whole or in part), wherein said plurality of lights or said mechanical stimuli further comprises a material adjacent to one or more of said plurality of lights or said mechanical stimuli or a portion of one or more of said plurality of lights or said mechanical stimuli, said material having one or more of the following qualities: light-absorbent, unreflective, less-reflective, anti-reflective, or a low reflexive index.

Example 30. The system according to example 1 (as well as subject matter of one or more of any combination of examples 2-29, in whole or in part), wherein said frame further comprises a circuit board, said circuit board in communication with said plurality of lights or said mechanical stimuli.

Example 31. The system according to example 30, wherein said processor or controller is in communication with said circuit board, wherein said circuit board is in communication with said plurality of lights, and wherein said processor or controller controls said circuit board.

Example 32. The system according to example 1 (as well as subject matter of one or more of any combination of examples 2-31, in whole or in part), further comprising a circuit board, wherein said circuit board is configured to be in hard-wired or wireless communication, so as to define circuit board hard-wired or wireless communication, with said plurality of lights or said mechanical stimuli.

Example 33. The system of example 32, wherein said circuit board wireless communication between said circuit board and said plurality of lights or said mechanical stimuli comprises a transmitter and a receiver.

Example 34. The system according to example 32 (as well as subject matter in whole or in part of example 33), wherein said processor or controller is in communication with said circuit board, wherein said circuit board is in communication with said plurality of lights or said mechanical stimuli, and wherein said processor or controller controls said circuit board.

Example 35. The system according to example 1 (as well as subject matter of one or more of any combination of examples 2-34, in whole or in part), further comprising a computer interface configured to control said processor or controller in hard-wired or wireless communication with said plurality of lights or said mechanical stimuli to activate said plurality of lights or said mechanical stimuli in said specified order in accordance with a testing protocol.

Example 36. The system of example 35, wherein said specified order of activating said plurality of lights or said mechanical stimuli may include any one or more of the following: randomly, sequentially, serially, repeatedly, or in combination of said plurality of lights or said mechanical stimuli.

Example 37. The system of example 35 (as well as subject matter in whole or in part of example 36), wherein said specified order may include any one or more of the following:

either one or two of said plurality of lights or said mechanical stimuli are configured to activate simultaneously during said screening, and said plurality of lights or said mechanical stimuli are placed in communication with said frame in four quadrants that coincide with four quadrants of the said patient's vision and are programmed such that each quadrant of vision is tested at least once, in random order and at random intervals.

Example 38. The system according to example 1 (as well as subject matter of one or more of any combination of examples 2-37, in whole or in part), wherein said position is configured such that said plurality of lights or said mechanical stimuli are configured to be a specified number of degrees, $\theta$, from a pupil center of said eye of said patient, wherein said specified number of degrees, $\theta$, includes any one of the following:

about 24 degrees;
a range of about 23 degrees to about 25 degrees;
a range of about 22 degrees to about 26 degrees;
a range of about 18 degrees to about 30 degrees;
a range of about 24 degrees to about 34 degrees;
a range of about 0 degrees to about 30 degrees;
a range of about 0 degrees to about 60 degrees; or
a range of about 0 degrees to about 90 degrees.

Example 39. The system according to example 1 (as well as subject matter of one or more of any combination of examples 2-38, in whole or in part), wherein said position is configured such that said plurality of lights or said mechanical stimuli, closest to the nose of said patient, are configured to be a specified number of degrees, $\theta$, from a pupil center of said eye of said patient for each of said second eye and first eye of said patient;

wherein said frame is positioned at a specified orthogonal distance away from said patient's eyes and towards said one or more operators in an orthogonal direction from said patient's eyes;

wherein an overlap or intersection is defined as the point at which said specified number of degrees, $\theta$, from a pupil center of said eye of said patient for each said second eye and first eye of said patient, and towards the nose of said patient, overlaps or intersects; and wherein said specified orthogonal distance is less than the distance from said patient to said overlap or intersection and towards said one or more operators in an orthogonal direction.

Example 40. The system of example 1 (as well as subject matter of one or more of any combination of examples 2-39, in whole or in part), wherein said visual fields comprise one or more of any one of the following:

gross visual fields or peripheral visual fields.

Example 41. The system of example 1 (as well as subject matter of one or more of any combination of examples 2-40, in whole or in part), wherein said specified order is determined by said processor or controller and/or said one or more operators.

Example 42. The system of example 1 (as well as subject matter of one or more of any combination of examples 2-41, in whole or in part), further comprising a pupil finder structure in mechanical communication with said frame.

Example 43. The system of example 1 (as well as subject matter of one or more of any combination of examples 2-42, in whole or in part), wherein at least one of said plurality of lights is configured to cast enough light on a pupil of said one or both eyes of said patient to a) induce constriction or dilation to said pupils or b) to assess the reaction or inaction or no movement of said pupils, and said one or more operators is capable of observing said reaction.

Example 44. The system of example 1 (as well as subject matter of one or more of any combination of examples 2-43, in whole or in part), wherein said frame is positioned:

at least about 12 mm away from said patient's eyes and towards said one or more operators in an orthogonal direction from said patient's eyes;

at least about 15 mm away from said patient's eyes and towards said one or more operators in an orthogonal direction from said patient's eyes;

between and inclusive of about 12 and about 15 mm away from patient's eyes and towards said one or more operators in an orthogonal direction from said patient's eyes;

between and inclusive of about 10 and about 20 mm away from patient's eyes and towards said one or more operators in an orthogonal direction from said patient's eyes;

between and inclusive of about 10 and about 12 mm away from patient's eyes and towards said one or more operators in an orthogonal direction from said patient's eyes;

between and inclusive of about 1 and about 6 mm away from patient's eyes and towards said one or more operators in an orthogonal direction from said patient's eyes;

between and inclusive of about 6 and about 10 mm away from patient's eyes and towards said one or more operators in an orthogonal direction from said patient's eyes;

between and inclusive of about 20 and about 40 mm away from patient's eyes and towards said one or more operators in an orthogonal direction from said patient's eyes;

between and inclusive of about 1 and about 40 mm away from patient's eyes and towards said one or more operators in an orthogonal direction from said patient's eyes;

between and inclusive of about 40 and about 56 mm away from patient's eyes and towards said one or more operators in an orthogonal direction from said patient's eyes;

between and inclusive of about 56 and about 84 mm away from patient's eyes and towards said one or more operators in an orthogonal direction from said patient's eyes; or between and inclusive of about 84 and about 138 mm away from patient's eyes and towards said one or more operators in an orthogonal direction from said patient's eyes.

Example 45. A method for performing rapid, interactive screening of visual fields comprising:

providing a system for performing said rapid, interactive screening of visual fields on a patient, wherein said system is configured to be placed on said patient such that one or more of said patient's eyes are directly observable by one or more operators relative to a vantage point located in front of said patient;

providing instructions to said patient for said patient to provide feedback when one or more lights or mechanical stimuli on said system are activated, wherein said one or more lights or said mechanical stimuli are disposed in a position, wherein said position allows for the testing of a patient's visual fields;

activating said lights or said mechanical stimuli, using a processor or controller, in one or more specified orders, wherein said one or more specified orders is in accordance with a testing protocol; and wherein said system is configured to allow said operator to be positioned at said vantage point to allow said operator to substantially simultaneously observe:

one or both of said patient's eyes;

one or more of said lights or said mechanical stimuli activated; and the feedback provided by said patient.

Example 46. The method according to example 45, wherein said operator determines whether said feedback provided by said patient indicates said patient observed said one or more lights or said mechanical stimuli activated.

Example 47. The method of example 46, wherein said operator determines whether:

said feedback provided by said patient indicates no activated lights or mechanical stimuli were missed;

said feedback provided by said patient indicates quadrantanopsia or partial quadrantanopsia;

said feedback provided by said patient indicates hemianopsia; or said feedback provided by said patient indicates peripheral blindness.

Example 48. The method of example 46 (as well as subject matter in whole or in part of example 47), wherein based on the feedback provided by said patient the condition of the patient is determined to be one of the following:

said patient is without deficiency of detecting all quadrants of one or both eyes;

said patient is deficient in one quadrant of one or both eyes;

said patient is deficient in two quadrants of one or both eyes; or said patient is deficient in four quadrants of one or both eyes.

Example 49. The method according to example 45 (as well as subject matter of one or more of any combination of examples 46-48, in whole or in part), wherein said system allows said operator to evaluate the result of said observations for the existence of one or more gross visual field deficits.

Example 50. The method according to example 45 (as well as subject matter of one or more of any combination of examples 46-49, in whole or in part), wherein said processor further comprises a computer or microcontroller.

Example 51. The method of example 45 (as well as subject matter of one or more of any combination of examples 46-50, in whole or in part), wherein said controller is a servomotor.

Example 52. The method according to example 45 (as well as subject matter of one or more of any combination of examples 46-51, in whole or in part), wherein said processor or controller may be configured or said system is configured to allow one or more operators to operate said processor so as to alter said one or more specified orders at a time that includes one or more of the following:

before, during, or after executing said one or more specified orders.

Example 53. The method according to said example 52, wherein said one or more specified orders of activating said plurality of lights or said mechanical stimuli may include any one or more of the following:

randomly, sequentially, serially, repeatedly, or in combination of said plurality of lights or said mechanical stimuli.

Example 54. The method according to example 45 (as well as subject matter of one or more of any combination of examples 46-53, in whole or in part), wherein said system is configured to allow said operator to repeat said activation of one or more lights or said mechanical stimuli when said feedback provided by said patient is unable to be observed by said operator.

Example 55. The method according to example 45 (as well as subject matter of one or more of any combination of examples 46-54, in whole or in part), further comprising using one or more feedback capturing devices, positioned in front of and facing said front of said frame, to directly observe one or both of the eyes of said patient.

Example 56. The method according to example 52 (as well as subject matter of one or more of any combination of examples 46-55, in whole or in part), wherein said one or more feedback capturing devices is in remote communication with a remote system or with said one or more operators located remotely.

Example 57. The method according to example 52 (as well as subject matter of one or more of any combination of examples 46-56, in whole or in part), wherein said feedback capturing device is a video recorder, an image capturing device or camera, or an image capturing device or camera with a microphone.

Example 58. The method according to example 56 (as well as subject matter of one or more of any combination of examples 46-55 and 57, in whole or in part), wherein said communication includes decryption and/or encryption.

Example 59. A method for performing rapid screening of visual field deficits of a patient, comprising:

instructing said patient to provide feedback when one or more visual stimuli are visible to said patient;

using an apparatus to display one or more visual stimuli in a peripheral visual field quadrant to said patient, while one or both of said patient's eyes are directly observable by an operator;

displaying said one or more visual stimuli in at least one of said remaining quadrants in a specified order, wherein said specified order in accordance with a testing protocol;

wherein said operator substantially simultaneously observes:

one or both of said patient's eyes;

one or more of said stimuli; and the feedback provided by said patient; and wherein said operator evaluates a result of said observations for one or more potential visual field deficits.

Example 60. The method according to example 59, wherein said specified order may include any one or more of the following:

either one or two of said visual stimuli are configured to activate simultaneously during said screening, and said visual stimuli configure to appear in one or more of four quadrants that coincide with four quadrants of said patient's vision such that each said quadrant of vision is tested at least once, in random order or at random intervals.

Example 61. The method according to example 59 (as well as subject matter in whole or in part of example 60), wherein said specified order of activating a plurality of said visual stimuli may include any one or more of the following: randomly, sequentially, serially, repeatedly, or in combination of said plurality of said visual stimuli.

Example 62. A method of manufacturing any one or more of the systems or sub-systems in any one or more of Examples 1-44.

Example 63. A method of using any one or more of the systems or sub-systems in any one or more of Examples 1-44.

Example 64. A system or sub-system configured for applying the methods in any one or more of Examples 45-61.

REFERENCES

The devices, systems, apparatuses, modules, compositions, materials, computer program products, non-transitory computer readable medium, and methods of various embodiments of the invention disclosed herein may utilize aspects (such as devices, apparatuses, modules, systems, compositions, materials, computer program products, non-transitory computer readable medium, and methods) disclosed in the following references, applications, publications and patents and which are hereby incorporated by reference herein in their entirety (and which are not admitted to be prior art with respect to the present invention by inclusion in this section).

A. U.S. Pat. No. 10,178,948 B2, Liu, et al., "Self Operable Ophthalmic Device", Jan. 15, 2019.

B. U.S. Pat. No. 9,895,057 B2, Tumlinson, "Functional Vision Testing Using Light Field Displays", Feb. 20, 2018.

C. U.S. Pat. No. 6,299,632 B1, Jaillet, "Method for Changing Critical Brain Activity Using Light and Sound", Oct. 9, 2001.

D. Dodgson, "Variation and Extrema of Human Interpupillary Distance", Proceedings of SPIE—The International Society for Optical Engineering 5291:36-46, January 2004.

E. U.S. Pat. No. 6,033,076, Braeuning, et al., "Visual Field Testing via Telemedicine", Mar. 7, 2000.

F. U.S. Pat. No. 5,946,075, Horn, "Vision Screening System", Aug. 31, 1999.

G. U.S. Pat. No. 8,583,223 B2, Maddess, et al., "Assessment of Neural Function", Nov. 12, 2013.

H. U.S. Pat. No. 8,807,753 B2, Maddess, et al., "Pupillary Assessment Method and Apparatus", Aug. 19, 2014.

I. U.S. Pat. No. 10,064,548 B2, Maddess, et al., "Method and Apparatus for Sensory Field Assessment", Sep. 4, 2018.

J. U.S. Pat. No. 9,848,771 B2, Maddess, et al., "Clustered Volley Method and Apparatus", Dec. 26, 2017.

K. U.S. Pat. No. 7,594,728 B2, Seal, et al., "Adjustable Device for Vision Testing and Therapy", Sep. 29, 2009.

L. U.S. Pat. No. 7,278,742 B2, Manahilov, Systems and Apparatus for Assessment of Visual Field Functions, Oct. 9, 2007.

M. U.S. Pat. No. 8,851,678 B2, Pelah, et al., Visual Perimeter Measurement System and Method, Oct. 7, 2014.

N. International Patent Appl. Publ. No. WO 1995/029627 A1, Maddess, Method and Apparatus for Early Detection of Glaucoma, Nov. 9, 1995.

O. U.S. Pat. No. 10,143,367 B2, Gonzalez de la Rosa, Instrument and Method for Visual Field Examination, Dec. 4, 2018.

P. U.S. Pat. No. 9,629,538 B2, Wang, Contour Integration Perimetry Vision Test, Apr. 25, 2017.

Q. U.S. Pat. No. 8,931,905 B2, Lewis, Binocular Measurement Method and Device, Jan. 13, 2015.

R. U.S. Pat. No. 7,220,000 B2, Alster, et al. Methods, Devices and Systems for Assessing Eye Disease, May 22, 2007.

S. U.S. Patent Appl. Publ. No, 2020/0041797 A1, Samec, et al., Augmented and Virtual Reality Display Systems and Methods for Diagnosing Health Conditions Based on Visual Fields, Feb. 6, 2020.

T. U.S. Pat. No. 9,619,613 B2, Meyer, et al., Device and Methods for Mobile Monitoring and Assessment of Clinical Function through Sensors and Interactive Patient Responses, Apr. 11, 2017.

U. U.S. Pat. No. 9,823,808 B2, Crain, et al., Methods and Devices for Recording Changes in Visual Stimuli Observed through Browser-Based Interfaces, Nov. 21, 2017.

V. U.S. Patent Appl. Publ. No. 2007/0038142 A1, Todd, et al., Method and Device for Delivering Visual Stimuli with Head Mounted Display During vision Training, Feb. 15, 2007.

W. U.S. Pat. No. 7,309,315 B2, Kullok, et al., Apparatus, Method and Computer Program Product to Facilitate Ordinary Visual Perception via an Early Perceptual-Motor Extraction of Relational Information from a Light Stimuli Array to Trigger an Overall Visual-Sensory Motor Integration in a Subject, Dec. 18, 2007.

X. U.S. Pat. No. 6,475,162 B1, Hu, System and Method for Vision Examination Using Interrupt Signals for Synchronizing Visual Evoked Potential Sampling Rate with Visual Stimulus, Nov. 5, 2002.

Y. U.S. Pat. No. 9,625,989 B2, Wilson, et al., Head Mounted Display, Apr. 18, 2017.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particular interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A system for performing rapid, interactive screening of visual fields of a patient, comprising:
   a frame having a front and a back, wherein said back of said frame is configured to directionally face said patient and said front of said frame is opposite said back of said frame and is configured to directionally face one or more operators;
   said frame configured to allow a vantage point adjacent to and in front of said front of said frame to allow direct observation of one or both eyes of said patient;
   a plurality of lights or mechanical stimuli in mechanical communication with said frame, wherein upon activation of said plurality of lights or said mechanical stimuli, said plurality of lights or said mechanical stimuli are configured to be directly visible by said patient and said one or more operators, and wherein said plurality of lights or said mechanical stimuli are disposed in a position, wherein said position allows for the testing of a patient's visual fields; and
   said plurality of lights or said mechanical stimuli are configured to be in hard-wired or wireless communication with a processor or controller and said plurality of lights or said mechanical stimuli are configured to activate in a specified order, wherein said specified order is in accordance with a testing protocol.

2. The system of claim 1, wherein said specified order of activating said plurality of lights or said mechanical stimuli may include any one or more of the following:
   randomly, sequentially, serially, repeatedly, or in combination of said plurality of lights or mechanical stimuli.

3. The system of claim 1, wherein said specified order includes:
   either one or two of said plurality of lights or said mechanical stimuli are configured to activate simultaneously during said screening, and said plurality of lights or said mechanical stimuli are placed in communication with said frame in four quadrants that coincide with four quadrants of said patient's vision and are programmed such that each said quadrant of vision is tested at least once, in random order and/or at random intervals.

4. The system of claim 1, wherein said specified order of activating said plurality of lights or said mechanical stimuli is configured to activate on a first side of said frame in relation to one of said eyes or on a first side and a second side of said frame wherein each of said first and second sides of said frame correspond respectively with a first said eye and a second said eye.

5. The system of claim 1, further comprising a kit, wherein said kit comprises:
   said processor or controller configured so as to be able to be in electrical communication with said plurality of lights or said mechanical stimuli, wherein said processor or controller is configured so as to be able to control said activation of said plurality of lights or said mechanical stimuli in the specified order, wherein said specified order is in accordance with said testing protocol.

6. The system of claim 1, further comprising:
said processor or controller in electrical communication with said plurality of lights or said mechanical stimuli, wherein said processor or controller is configured to control said activation of said plurality of lights or said mechanical stimuli in said specified order, wherein said specified order is in accordance with said testing protocol.

7. The system of claim 1, wherein said processor comprises a microcontroller.

8. The system of claim 1, wherein said controller is a servomotor.

9. The system of claim 1, further comprising at least one stabilizer structure in mechanical communication with said frame.

10. The system of claim 9, wherein said at least one stabilizer structure comprises a vertical stabilizer and/or a horizontal stabilizer.

11. The system of claim 9, wherein said at least one stabilizer structure comprises at least one or more of any one of the following: a nasion brace, one or two temples, or at least one strap.

12. The system of claim 1, wherein said hard-wired communication between said plurality of lights or said mechanical stimuli and said processor or controller extends within or along at least one temple.

13. The system of claim 1, wherein said wireless communication between said plurality of lights or said mechanical stimuli and said processor or controller comprises a transmitter and a receiver.

14. The system of claim 13, wherein said transmitter and/or said receiver are configured to be in electrical communication with a power source.

15. The system of claim 1, wherein said plurality of lights or said mechanical stimuli are disposed on said frame.

16. The system of claim 1, further comprising:
a lens disposed within said frame, wherein said plurality of lights or said mechanical stimuli are disposed on or within said lens.

17. The system of claim 1, wherein said system is configured to allow remote communication for one or more operators to communicate with said patient.

18. The system of claim 1, wherein said vantage point allows said one or more operators, in front of said front of said frame, to directly observe one or both of the eyes of said patient.

19. The system of claim 18, wherein said vantage point allows one or more feedback capturing devices, positioned in front of and facing said front of said frame, to directly observe one or both of the eyes of said patient.

20. The system of claim 19, wherein said one or more feedback capturing devices is in remote communication with a remote system or with said one or more operators located remotely.

21. The system according to claim 20, wherein said remote communication includes decryption and/or encryption.

22. The system of claim 19, wherein said feedback capturing device is a video recorder, an image capturing device or camera, or an image capturing device or camera with a microphone.

23. The system of claim 1, wherein said vantage point allows one or more image feedback capturing devices, in front of said front of said frame, to directly observe one or both of the eyes of said patient.

24. The system of claim 23, wherein said one or more feedback capturing devices is in remote communication with a remote system or with said one or more operators located remotely.

25. The system of claim 24, wherein said feedback capturing device is a video recorder, an image capturing device or camera, or an image capturing device or camera with a microphone.

26. The system of claim 1, further comprising a power source configured to be in communication with said processor or controller and/or said plurality of lights or said mechanical stimuli.

27. The system of claim 1, wherein said plurality of lights include any one or more of the following: LED light, fiber optic light, pinpoint-type light, or small target light.

28. The system of claim 1, wherein said plurality of said mechanical stimuli include any one or more of the following:
mechanical device configured to provide a black and white target, color target, sign, symbol, figurine, bust, sculpture, or a picture.

29. The system according to claim 1, wherein said plurality of lights or said mechanical stimuli further comprises a material adjacent to one or more of said plurality of lights or said mechanical stimuli or a portion of one or more of said plurality of lights or said mechanical stimuli, said material having one or more of the following qualities: light-absorbent, unreflective, less-reflective, anti-reflective, or a low reflexive index.

30. The system according to claim 1, wherein said frame further comprises a circuit board, said circuit board in communication with said plurality of lights or said mechanical stimuli.

31. The system according to claim 30, wherein said processor or controller is in communication with said circuit board, wherein said circuit board is in communication with said plurality of lights, and wherein said processor or controller controls said circuit board.

32. The system according to claim 1, further comprising a circuit board, wherein said circuit board is configured to be in hard-wired or wireless communication, so as to define circuit board hard-wired or wireless communication, with said plurality of lights or said mechanical stimuli.

33. The system of claim 32, wherein said circuit board wireless communication between said circuit board and said plurality of lights or said mechanical stimuli comprises a transmitter and a receiver.

34. The system according to claim 32, wherein said processor or controller is in communication with said circuit board, wherein said circuit board is in communication with said plurality of lights or said mechanical stimuli, and wherein said processor or controller controls said circuit board.

35. The system according to claim 1, further comprising a computer interface configured to control said processor or controller in hard-wired or wireless communication with said plurality of lights or said mechanical stimuli to activate said plurality of lights or said mechanical stimuli in said specified order in accordance with a testing protocol.

36. The system of claim 35, wherein said specified order of activating said plurality of lights or said mechanical stimuli may include any one or more of the following:

randomly, sequentially, serially, repeatedly, or in combination of said plurality of lights or said mechanical stimuli.

37. The system of claim 35, wherein said specified order may include any one or more of the following:

either one or two of said plurality of lights or said mechanical stimuli are configured to activate simultaneously during said screening, and said plurality of lights or said mechanical stimuli are placed in communication with said frame in four quadrants that coincide with four quadrants of the said patient's vision and are programmed such that each quadrant of vision is tested at least once, in random order and at random intervals.

38. The system according to claim 1, wherein said position is configured such that said plurality of lights or said mechanical stimuli are configured to be a specified number of degrees, θ, from a pupil center of said eye of said patient, wherein said specified number of degrees, θ, includes any one of the following:

about 24 degrees;

a range of about 23 degrees to about 25 degrees;

a range of about 22 degrees to about 26 degrees;

a range of about 18 degrees to about 30 degrees;

a range of about 24 degrees to about 34 degrees;

a range of about 0 degrees to about 30 degrees;

a range of about 0 degrees to about 60 degrees; or a range of about 0 degrees to about 90 degrees.

39. The system according to claim 1, wherein said position is configured such that said plurality of lights or said mechanical stimuli, closest to the nose of said patient, are configured to be a specified number of degrees, θ, from a pupil center of said eye of said patient for each of said second eye and first eye of said patient;

wherein said frame is positioned at a specified orthogonal distance away from said patient's eyes and towards said one or more operators in an orthogonal direction from said patient's eyes;

wherein an overlap or intersection is defined as the point at which said specified number of degrees, θ, from a pupil center of said eye of said patient for each said second eye and first eye of said patient, and towards the nose of said patient, overlaps or intersects; and wherein said specified orthogonal distance is less than the distance from said patient to said overlap or intersection and towards said one or more operators in an orthogonal direction.

40. The system of claim 1, wherein said visual fields comprise one or more of any one of the following:

gross visual fields or peripheral visual fields.

41. The system of claim 1, wherein said specified order is determined by said processor or controller and/or said one or more operators.

42. The system of claim 1, further comprising a pupil finder structure in mechanical communication with said frame.

43. The system of claim 1, wherein at least one of said plurality of lights is configured to cast enough light on a pupil of said one or both eyes of said patient to a) induce constriction or dilation to said pupils or b) to assess the reaction or inaction or no movement of said pupils, and said one or more operators is capable of observing said reaction.

44. The system of claim 1, wherein said frame is positioned:

at least about 12 mm away from said patient's eyes and towards said one or more operators in an orthogonal direction from said patient's eyes;

at least about 15 mm away from said patient's eyes and towards said one or more operators in an orthogonal direction from said patient's eyes;

between and inclusive of about 12 and about 15 mm away from patient's eyes and towards said one or more operators in an orthogonal direction from said patient's eyes;

between and inclusive of about 10 and about 20 mm away from patient's eyes and towards said one or more operators in an orthogonal direction from said patient's eyes;

between and inclusive of about 10 and about 12 mm away from patient's eyes and towards said one or more operators in an orthogonal direction from said patient's eyes;

between and inclusive of about 1 and about 6 mm away from patient's eyes and towards said one or more operators in an orthogonal direction from said patient's eyes;

between and inclusive of about 6 and about 10 mm away from patient's eyes and towards said one or more operators in an orthogonal direction from said patient's eyes;

between and inclusive of about 20 and about 40 mm away from patient's eyes and towards said one or more operators in an orthogonal direction from said patient's eyes;

between and inclusive of about 1 and about 40 mm away from patient's eyes and towards said one or more operators in an orthogonal direction from said patient's eyes;

between and inclusive of about 40 and about 56 mm away from patient's eyes and towards said one or more operators in an orthogonal direction from said patient's eyes;

between and inclusive of about 56 and about 84 mm away from patient's eyes and towards said one or more operators in an orthogonal direction from said patient's eyes; or between and inclusive of about 84 and about 138 mm away from patient's eyes and towards said one or more operators in an orthogonal direction from said patient's eyes.

45. A method for performing rapid, interactive screening of visual fields of a patient, comprising:

providing a system for performing said rapid, interactive screening of visual fields on said patient, wherein said system is configured to be placed on said patient such that one or more of said patient's eyes are directly observable by one or more operators relative to a vantage point located in front of said patient;

providing instructions to said patient for said patient to provide feedback when one or more lights or mechanical stimuli on said system are activated, wherein said one or more lights or said mechanical stimuli are disposed in a position, wherein said position allows for the testing of a patient's visual fields;

activating said lights or said mechanical stimuli, using a processor or controller, in one or more specified orders, wherein said one or more specified orders is in accordance with a testing protocol; and wherein said system is configured to allow said operator to be positioned at said vantage point to allow said operator to substantially simultaneously observe:

one or both of said patient's eyes;

one or more of said lights or said mechanical stimuli activated; and the feedback provided by said patient.

46. The method according to claim 45, wherein said operator determines whether said feedback provided by said patient indicates said patient observed said one or more lights or said mechanical stimuli activated.

47. The method of claim 46, wherein said operator determines whether:

said feedback provided by said patient indicates no activated lights or mechanical stimuli were missed;

said feedback provided by said patient indicates quadrantanopsia or partial quadrantanopsia;

said feedback provided by said patient indicates hemianopsia; or said feedback provided by said patient indicates peripheral blindness.

48. The method of claim 46, wherein based on the feedback provided by said patient the condition of the patient is determined to be one of the following:

said patient is without deficiency of detecting all quadrants of one or both eyes;

said patient is deficient in one quadrant of one or both eyes;

said patient is deficient in two quadrants of one or both eyes; or said patient is deficient in four quadrants of one or both eyes.

49. The method according to claim 45, wherein said system allows said operator to evaluate the result of said observations for the existence of one or more gross visual field deficits.

50. The method according to claim 45, wherein said processor further comprises a computer or microcontroller.

51. The method of claim 45, wherein said controller is a servomotor.

52. The method according to claim 45, wherein said processor or controller may be configured or said system is configured to allow one or more operators to operate said processor so as to alter said one or more specified orders at a time that includes one or more of the following:

before, during, or after executing said one or more specified orders.

53. The method according to said claim 52, wherein said one or more specified orders of activating said plurality of lights or said mechanical stimuli may include any one or more of the following:

randomly, sequentially, serially, repeatedly, or in combination of said plurality of lights or said mechanical stimuli.

54. The method according to claim 45, wherein said system is configured to allow said operator to repeat said activation of one or more lights or said mechanical stimuli when said feedback provided by said patient is unable to be observed by said operator.

55. The method according to claim 45, further comprising using one or more feedback capturing devices, positioned in front of and facing said front of said frame, to directly observe one or both of the eyes of said patient.

56. The method according to claim 52, wherein said one or more feedback capturing devices is in remote communication with a remote system or with said one or more operators located remotely.

57. The method according to claim 52, wherein said feedback capturing device is a video recorder, an image capturing device or camera, or an image capturing device or camera with a microphone.

58. The method according to claim 56, wherein said communication includes decryption and/or encryption.

59. A method for performing rapid screening of visual field deficits of a patient, comprising:

instructing said patient to provide feedback when one or more visual stimuli are visible to said patient;

using an apparatus to display one or more visual stimuli in a peripheral visual field quadrant to said patient, while one or both of said patient's eyes are directly observable by an operator;

displaying said one or more visual stimuli in at least one of said remaining quadrants in a specified order, wherein said specified order in accordance with a testing protocol;

wherein said operator substantially simultaneously observes:

one or both of said patient's eyes;

one or more of said stimuli; and the feedback provided by said patient; and wherein said operator evaluates a result of said observations for one or more potential visual field deficits.

60. The method according to claim 59, wherein said specified order may include any one or more of the following:

either one or two of said visual stimuli are configured to activate simultaneously during said screening, and said visual stimuli configure to appear in one or more of four quadrants that coincide with four quadrants of said patient's vision such that each said quadrant of vision is tested at least once, in random order or at random intervals.

61. The method according to claim 59, wherein said specified order of activating a plurality of said visual stimuli may include any one or more of the following:

randomly, sequentially, serially, repeatedly, or in combination of said plurality of said visual stimuli.

\* \* \* \* \*